(12) United States Patent
Sharma et al.

(10) Patent No.: US 10,993,919 B2
(45) Date of Patent: May 4, 2021

(54) CHONDROPROTECTIVE NANOPARTICLES FOR THE TREATMENT OF OSTEOARTHRITIS

(71) Applicant: University of Florida Research Foundation, Inc., Gainesville, FL (US)

(72) Inventors: Blanka Sharma, Gainesville, FL (US); Shannon B. Brown, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

(21) Appl. No.: 16/337,142

(22) PCT Filed: Oct. 3, 2017

(86) PCT No.: PCT/US2017/054911
§ 371 (c)(1),
(2) Date: Mar. 27, 2019

(87) PCT Pub. No.: WO2018/067545
PCT Pub. Date: Apr. 12, 2018

(65) Prior Publication Data
US 2019/0224132 A1  Jul. 25, 2019

Related U.S. Application Data

(60) Provisional application No. 62/542,947, filed on Aug. 9, 2017, provisional application No. 62/403,819, filed on Oct. 4, 2016.

(51) Int. Cl.
*A61K 9/51* (2006.01)
*A61K 38/18* (2006.01)
(Continued)

(52) U.S. Cl.
CPC .......... *A61K 9/5153* (2013.01); *A61K 9/0019* (2013.01); *A61K 9/5161* (2013.01);
(Continued)

(58) Field of Classification Search
CPC .............................. A61P 19/02; A61K 9/5153
See application file for complete search history.

(56) References Cited

U.S. PATENT DOCUMENTS

| 6,511,958 B1 * | 1/2003 | Atkinson | ............ A61F 2/30756 424/422 |
| 2003/0012765 A1 * | 1/2003 | Thompson | ............. A61K 9/146 424/85.1 |

(Continued)

FOREIGN PATENT DOCUMENTS

| CA | 2520475 A1 | 10/2004 | | |
| WO | WO-9908728 A1 * | 2/1999 | ........... | A61L 27/227 |
| WO | WO-2016032148 A2 * | 3/2016 | ............. | A61K 47/61 |

OTHER PUBLICATIONS

ML Kang, J-Y Ko, JE Kim, G-I Im. "Intra-articular delivery of kartogenin-conjugated chitosan nano/microparticles for cartilage regeneration." Biomaterials, vol. 35, 2014, pp. 9984-9994. (Year: 2014).*

(Continued)

*Primary Examiner* — Isaac Shomer
(74) *Attorney, Agent, or Firm* — Thomas|Horstemeyer LLP

(57) ABSTRACT

Compositions and methods are disclosed herein to deliver and anchor nanoscale drug carriers into the extracellular matrix (ECM) of tissues, such as degenerating cartilage or tumor margins, and to provide local and sustained release of drugs.

11 Claims, 15 Drawing Sheets

Specification includes a Sequence Listing.

(51) Int. Cl.
    *A61K 31/192* (2006.01)
    *A61K 9/00* (2006.01)
    *A61P 19/02* (2006.01)
    *B82Y 5/00* (2011.01)
    *A61P 35/00* (2006.01)

(52) U.S. Cl.
    CPC ........ *A61K 31/192* (2013.01); *A61K 38/1858* (2013.01); *A61P 19/02* (2018.01); *A61P 35/00* (2018.01); *B82Y 5/00* (2013.01)

(56) References Cited

U.S. PATENT DOCUMENTS

| | | | | |
|---|---|---|---|---|
| 2004/0072793 | A1* | 4/2004 | Aeschlimann | A61K 31/728 514/54 |
| 2008/0081074 | A1* | 4/2008 | Gu | A61K 9/5153 424/489 |
| 2009/0022777 | A1 | 1/2009 | Mathiowitz et al. | |
| 2010/0249156 | A1* | 9/2010 | Caramella | A61K 9/0034 514/263.37 |
| 2010/0297218 | A1 | 11/2010 | Gong et al. | |
| 2012/0142787 | A1* | 6/2012 | Lu | C08B 37/00 514/778 |
| 2014/0017263 | A1* | 1/2014 | Vyavahare | A61K 9/5146 424/178.1 |
| 2016/0213814 | A1* | 7/2016 | Berlowitz | A61L 27/24 |
| 2017/0290791 | A1* | 10/2017 | Im | A61K 47/61 |

OTHER PUBLICATIONS

D Shi, X Xu, Y Ye, K Song, Y Cheng, J Di, Q Hu, J Li, H Ju, Q Jiang, Z Gu. "Photo-Cross-Linked Scaffold with Kartogenin-Encapsulated Nanoparticles for Cartilage Regeneration." ACS Nano, vol. 10, 2016, pp. 1292-1299, published Jan. 12, 2016. (Year: 2016).*

Y Parajo, I d'Angelo, A Welle, M Garcia-Fuentes, MJ Alonso. "Hyaluronic acid/Chitosan nanoparticles as delivery vehicles for VEGF and PDGF-BB." Drug Delivery, vol. 17(8), 2010, pp. 596-604. (Year: 2010).*

D-A Wang, S Varghese, B Sharma, I Strehin, S Fermanian, J Gorham, DH Fairbrother, B Cascio, JH Elisseeff. "Multifunctional chondroitin sulphate for cartilage tissue—biomaterial integration." Nature Materials, vol. 6, May 2007, pp. 385-392. (Year: 2007).*

JMG Reyes, S Herretes, A Pirouzmanesh, D-A Wang, JH Elisseeff, A Jun, PJ McDonnell, RS Chuck, A Behrens. "A Modified Chondroitin Sulfate Aldehyde Adhesive for Sealing Corneal Incisions." Investigative Ophthalmology & Visual Science, vol. 46 No. 4, Apr. 2005, pp. 1247-1250. (Year: 2005).*

Gregory M. Cruise, David S. Scharp, Jeffrey A. Hubbell. "Characterization of permeability and network structure of interfacially photopolymerized poly(ethylene glycol) diacrylate hydrogels." Biomaterials, vol. 19, 1998, pp. 1287-1294. (Year: 1998).*

Chun-Jui Lin et al. "Integrated self-assembling drug delivery system possessing dual responsive and active targeting for orthotopic ovarian cancer theranostics." Biomaterials, vol. 90, 2016, pp. 12-26. (Year: 2016).*

Hongkee Sah Laura A Thoma, Hari R Desu, Edel Sah, George C. Wood. "Concepts and practices used to develop functional PLGA-based nanoparticulate systems." International Journal of Nanomedicine, vol. 8, 2013, pp. 747-765. (Year: 2013).*

David J. Mooney and Eduardo A. Silva. "A glue for biomaterials." Nature Materials, vol. 6, May 2007, pp. 327-328. (Year: 2007).*

Huaping Tan, Constance R. Chu, Karin A. Payne, Kacey G. Marra. "Injectable in situ forming biodegradable chitosan-hyaluronic acid based hydrogels for cartilage tissue engineering." Biomaterials 30 (2009), pp. 2499-2506. (Year: 2009).*

International Search Report, issued for PCT/US2017/054911, dated Jan. 2, 2018.

* cited by examiner

SEQUENCE LISTING

<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1

Trp Tyr Arg Gly Arg Leu Lys
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct

<400> SEQUENCE: 2

Gly Ala His Trp Gln Phe Asn Ala Leu Thr Val Arg
1               5                   10

CHONDROPROTECTIVE NANOPARTICLES FOR THE TREATMENT OF OSTEOARTHRITIS

CROSS-REFERENCE TO RELATED APPLICATIONS

This application claims benefit of U.S. Provisional Application No. 62/403,819, filed Oct. 4, 2016, and Application Ser. No. 62/542,947, filed Aug. 9, 2017, which are hereby incorporated herein by reference in their entirety.

STATEMENT REGARDING FEDERALLY SPONSORED RESEARCH OR DEVELOPMENT

This invention was made with Government Support under Grant No. TR001427 awarded by the National Institutes of Health. The Government has certain rights in the invention.

BACKGROUND

Advances in stem cell research have uncovered exciting possibilities for the treatment of a vast array of medical conditions and diseases. Unfortunately, stem cells injected or implanted into the body have demonstrated highly variable results in clinical trials. All adult tissues harbor stem cells that can contribute to tissue homeostasis and repair. Therapeutic approaches harnessing the regenerative potential of endogenous cells could circumvent the issues that hinder the success and reproducibility of exogenous stem cell transplantation, such as the burdensome and costly process of expansion and poor survival and engraftment in vivo.

Arthritis is the leading cause of disability in the U.S. and the fourth leading cause worldwide. The most common and disabling type of arthritis is osteoarthritis (OA), or degenerative joint disease, which affects 27 million people in the U.S., and is associated with healthcare expenditures of over $185 billion. These numbers are expected to grow as the population ages, reaching 67 million Americans by 2030. The physical limitations caused by OA contribute to high incidences of heart disease, depression and obesity. There is no cure for OA—current therapies are simply palliative, often requiring long-term use of pain medications that can have serious, life threatening side effects. There is a critical need for regenerative medicines that treat and/or prevent OA.

OA is a complex disease, marked primarily by articular cartilage degeneration that ultimately results in joint failure. The limited regenerative potential of articular cartilage is a central problem for degenerative joint disease, which is largely attributed to insufficient progenitor cell numbers and activity (Candela, M. E., et al. Matrix biology 39:44-49 (2014)). Therefore, injury- or disease-associated chondrocyte death eventually produces degenerative changes in the joint. Numerous small molecule drugs and trophic factors have been identified for promoting cartilage repair and blocking various OA disease mechanisms, however the success of these therapies have been significantly hindered by their short residence times in the joint and poor tissue targeting (Evans, C. H., et al. Nature reviews. Rheumatology 10:11-22 (2014)).

SUMMARY

Intra-articular injection of arthritis drugs into the joint can improve bioavailability and reduce systemic toxicity of the drugs. However, small molecule drugs as well as macromolecules are rapidly cleared (20 min for small molecules, 1-4 hrs for macromolecules) from the joint via small blood vessels and the lymphatics in the synovium, respectively (Evans, C. H., et al. Nature reviews. Rheumatology 10:11-22 (2014)), resulting in low drug-tissue interaction and poor efficacy.

Compositions and methods are disclosed herein to deliver and anchor nanoscale drug carriers into the extracellular matrix (ECM) of tissues, such as degenerating cartilage, to provide local and sustained release of drugs, such as OA drugs. Enhanced targeting and retention of drugs in the tissue, such as cartilage, improves their efficacy. In particular embodiments, the compositions and methods involve site-specific delivery of chondroinductive agents in order to replenish lost or dying chondrocytes and slow or reverse the degenerative changes in the joint. In some embodiments, the compositions and methods involve site-specific delivery of anti-cancer drugs near tumor margins, thereby eradicating remaining cancer cells.

A drug delivery system is therefore disclosed that comprises a therapeutic or diagnostic agent contained within a delivery vehicle and an effective amount of a bioadhesive to adhere and seed the delivery vehicle to a tissue in a subject. For example, the drug delivery system can comprises a chondrogenic or chondroprotective agent contained within a delivery vehicle and an effective amount of a bioadhesive to adhere and seed the delivery vehicle to cartilage in the joint of a subject. As another example, the drug delivery system can comprises anti-cancer agents contained within a delivery vehicle and an effective amount of a bioadhesive to adhere and seed the delivery vehicle to tumor margins in a subject.

In some embodiments, the chondrogenic or chondroprotective agent comprises Kartogenin. In some embodiments, the chondrogenic or chondroprotective agent comprises platelet-derived growth factor (PDGF-BB). In some embodiments, the chondrogenic or chondroprotective agent comprises antioxidants, anti-catabolic agents (eg. MMP inhibitors), or anabolic agents.

Suitable tumors could include any solid tumor that is accessible surgically, including breast, lung, prostate, pancreatic, colorectal, and brain. Suitable anti-cancer agents include chemotherapeutic agents such as paclitaxel and doxorubicin, or biologic agents such as DNA (e.g. plasmid DNA for wild type p53), microRNAs, or peptides.

The bioadhesive can be any natural or synthetic molecule capable of binding to cartilage in a joint. In some embodiments, the bioadhesive comprises chondroitin sulfate aldehyde (CSAld). In some embodiments, the bioadhesive comprises aldehyde functionalized hyaluronic acid. In some embodiments, the bioadhesive comprises polyethylene glycol.

In some embodiments, the delivery vehicle comprises a nanoparticle. In particular embodiments, the nanoparticle has a mean diameter ranging from 30 nanometers to 300 nm, including 30 to 100 nm, 50-300 nm, and 50-100 nm.

The nanoparticle can be any natural or synthetic biocompatible particle suitable for delivery of the chondrogenic or chondroprotective agent. In particular embodiments, the nanoparticle is biodegradable. In some embodiments, the nanoparticles are formed from a polymer selected from the group consisting of hyaluronan, chitosan, collagen, gelatin, alginate, polylactic acid (PLLA), polyglycolic acid (PGA), poly(lactic-co-glycolic acid) (PLGA), poly(ethylene glycol), and chondroitin sulfate.

Also disclosed is a method for treating a cartilage-related condition in a subject that involves administering to a joint of the subject a first composition comprising a chondrogenic or chondroprotective agent contained within a delivery vehicle and a second composition comprising a bioadhesive in an effective amount of to adhere the delivery vehicle to a cartilage surface in the joint of the subject.

In some embodiments, the cartilage-related condition comprises osteoarthritis. For example, in some cases, the osteoarthritis is post-traumatic osteoarthritis.

In some embodiments, the first composition and the second composition are combined into a slurry and administered together. In other embodiments, the first composition and the second composition are administered sequentially. For example, in some cases, the first composition is administered to the joint prior to the second composition. Likewise, in other cases, the second composition is administered to the joint prior to the first composition.

In preferred embodiments, at least the second composition is painted directly on the cartilage surface of the subject. In some cases, the first composition and the second composition are combined into a slurry and painted together on the cartilage surface.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
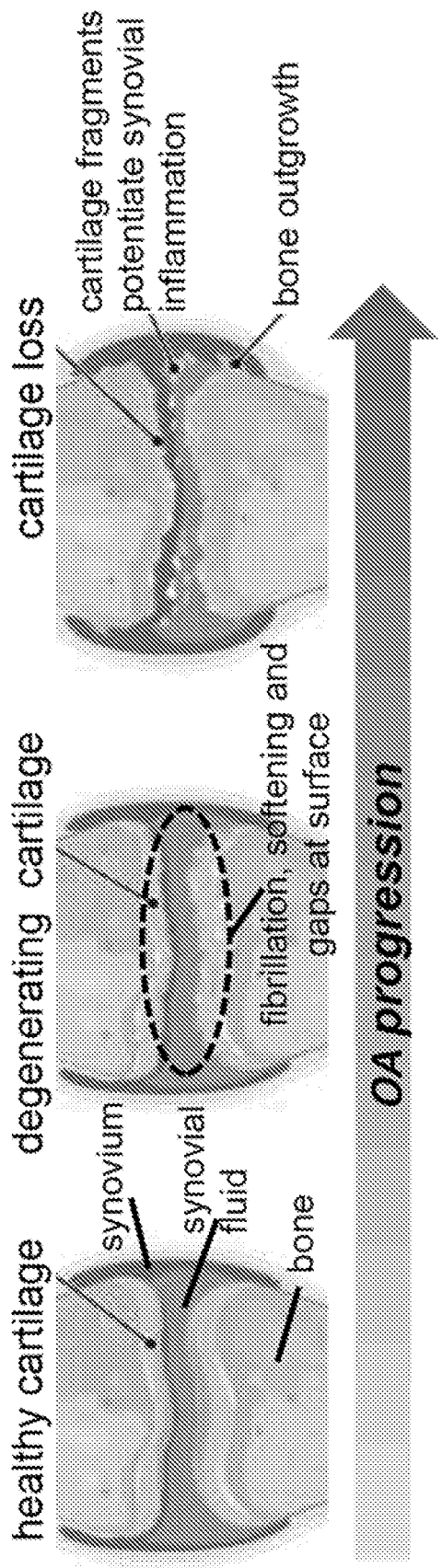
FIG. 1. The criteria for the design of a drug delivery system must consider the stage of disease and biochemical and physical characteristics of the cartilage. Chondroinduction at the early stage (middle) where cartilage is degenerating but not completely lost may serve to protect or reverse OA progression.

A drug delivery system is therefore disclosed that comprises a chondrogenic or chondroprotective agent contained within a delivery vehicle and an effective amount of a bioadhesive to adhere the delivery vehicle to a cartilage surface in the joint of a subject. Also disclosed is a method for treating a cartilage-related condition in a subject that involves administering to a joint of the subject a first composition comprising a chondrogenic or chondroprotective agent contained within a delivery vehicle and a second composition comprising a bioadhesive in an effective amount of to adhere the delivery vehicle to a cartilage surface in the joint of the subject.

Definitions

The term "cartilage-related condition" refers to any injury or defect in the articular cartilage. The term encompasses, but is not limited to, a rupture or detachment of the cartilage, a meniscal defect including a partial or complete tear, damage or a disease effecting the meniscus and/or patella, osteoarthritis (referred to herein as "OA"), including knee, finger, wrist, hip, ankle, elbow, toe, shoulder, and spinal osteoarthritis, traumatic cartilage rupture or detachment, ankylosing spondylitis, capsulitis, psoriatic arthritis, rheumatoid arthritis (RA), systemic lupus erythematosus, juvenile idiopathic arthritis, Chondropathy, Chondrosarcoma, Chondromalacia, Polychondritis, Relapsing Polychondritis, Slipped epiphysis, Osteochondritis Dissecans, Chondrodysplasia, Costochondritis, X-linked hypophosphatemic rickets, Osteochondroma, Chondrosarcoma (malignant), Osteoarthritis Susceptibility (types 1-6), Spondylosis, Osteochondroses, Primary chondrosarcoma, Chondrodysplasia, Tietze syndrome, Dermochondrocorneal dystrophy of Francois, Epiphyseal dysplasia, multiple, (types 1-5), Ossified Ear cartilages with Mental deficiency, Muscle Wasting and Bony Changes, Carpotarsal osteochondromatosis, Achondroplasia, Chondrocalcinosis (types 1-2), Genochondromatosis, Chondrodysplasia (disorder of sex development), Chondroma, Achondrogenesis (types 1A, 1B, 2, 3, 4, Langer-Saldino Type), Type II Achondrogenesis-Hypochondrogenesis, Atelosteogenesis, (type 1, 2 and III), Pyknoachondrogenesis, Pseudoachondroplasia, Osteoarthropathy of fingers, familial, Diastrophic dysplasia, Dyschondrosteosis-nephritis, Coloboma of Alar-nasal cartilages with telecanthus, Alar cartilages hypoplasia-coloboma-telecanthus, Pierre Robin syndrome-fetal chondrodysplasia, Dysspondyloenchondromatosis, Achondroplasia regional-dysplasia abdominal muscle, Osteochondritis Dissecans, Familial Articular Chondrocalcinosis, Tracheobronchomalacia, Chondritis, Dyschondrosteosis, Maffucci Syndrome, Jequier-Kozlowski-skeletal dysplasia, Chondrodystrophy, Cranio osteoarthropathy, Tietze's syndrome, Hip dysplasia-enchondromata-enchondromata, Bessel-Hagen disease, Chondromatosis (benign), Enchondromatosis (benign), chondrocalcinosis due to apatite crystal deposition, Meyenburg-Altherr-Uehlinger syndrome, Enchondromatosis-dwarfism-deafness, Astley-Kendall syndrome, Synovial osteochondromatosis, Chondrocalcinosis familial articular, Severe achondroplasia with developmental delay and acanthosis nigricans, Chondrocalcinosis, Keutel syndrome, Stanescu syndrome, Fibrochondrogenesis, Hypochondroplasia.

As used herein, the term "delivery vehicle" is intended to include all structures that contain, couple to or carry a therapeutic agent, such as nanospheres and other nanoparticles, microspheres and other microparticles, micelles and liposomes, including such vehicles formed of proteins, lipids, carbohydrates, synthetic organic compounds or inorganic compounds. Preferred delivery vehicles for the targeted systemic compositions of the present invention, described further below, are "particles," which is intended to include nanospheres and other nanoparticles, microspheres and other microparticles, micelles, and other delivery vehicles, but excluding liposomes which are less preferred as also described below. The term "delivery system" is intended to refer to a delivery vehicle and one or more contained or coupled therapeutic agents.

As used herein, the term "painting" refers to a method of administration that involves directly contacting the administration site with an agent and at least one bioadhesive in an amount effective to adhere the agent to the administration site.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder.

In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "agent" or "compound" as used herein refers to a chemical entity or biological product, or combination of chemical entities or biological products, administered to a subject to treat or prevent or control a disease or condition. The chemical entity or biological product is preferably, but not necessarily a low molecular weight compound, but may also be a larger compound, or any organic or inorganic molecule, including modified and unmodified nucleic acids such as antisense nucleic acids, RNAi, such as siRNA or shRNA, peptides, peptidomimetics, receptors, ligands, and antibodies, aptamers, polypeptides, nucleic acid analogues or variants thereof. For example, an agent can be an oligomer of nucleic acids, amino acids, or carbohydrates including, but not limited to proteins, peptides, oligonucleotides, ribozymes, DNAzymes, glycoproteins, RNAi agents (e.g., siRNAs), lipoproteins, aptamers, and modifications and combinations thereof. In some embodiments, an active agent is a nucleic acid, e.g., miRNA or a derivative or variant thereof. In some embodiments, an HB-X conjugate that comprises a nucleic acid agent, e.g., a RNAi or miRNA agent can be joined (e.g., conjugated) to HB peptide by means of a linker moiety can allow the miRNA or RNAi agent to interact with the DNA. In some embodiments, the linker moiety is a reversible moiety, e.g., miRNA or RNAi agent can be released from the HB peptide at the location of the target cell or tissue.

"Biocompatible" generally refers to a material and any metabolites or degradation products thereof that are generally non-toxic to the recipient and do not cause any significant adverse effects to the subject.

"Biodegradable" generally refers to a material that will degrade or erode under physiologic conditions to smaller units or chemical species that are capable of being metabolized, eliminated, or excreted by the subject. The degradation time is a function of polymer composition and morphology. Suitable degradation times are from days to months.

Chondroprotective/Chondroprotective Agents

In some embodiments, the chondrogenic or chondroprotective agent comprises Kartogenin. In some embodiments, the chondrogenic or chondroprotective agent comprises platelet-derived growth factor (PDGF-BB).

Additional representative chondroprotective agents include, for example: (1) antagonists of receptors for the interleukin-1 family of proteins, including, for example, IL-1β, IL-17 and IL-18; (2) antagonists of the tumor necrosis factor (TNF) receptor family, including, for example, TNF-R1; (3) agonists for interleukin 4, 10 and 13 receptors; (4) agonists for the TGF-β receptor superfamily, including, for example, BMP-2, BMP-4 and BMP-7; (5) inhibitors of COX-2; (6) inhibitors of the MAP kinase family, including, for example, p38 MAP kinase; (7) inhibitors of the matrix metalloproteinases (MMP) family of proteins, including, for example, MMP-3 and MMP-9; (8) inhibitors of the NF-κB family of proteins, including, for example, the p50/p65 dimer complex with IκB; (9) inhibitors of the nitric oxide synthase (NOS) family, including, for example, iNOS; (10)

agonists and antagonists of integrin receptors, including, for example, agonists of αVβ3 integrin; (11) inhibitors of the protein kinase C (PKC) family; (12) inhibitors of the protein tyrosine kinase family, including, for example, the src subfamily; (13) modulators of protein tyrosine phosphatases; and (14) inhibitors of protein src homology 2 (SH2) domains. Additional chondroprotective agents include other growth factors, such as by way of example insulin-like growth factors (e.g., IGF-1) and fibroblast growth factors (e.g., bFGF). In some embodiments, the chondrogenic or chondroprotective agent comprises epigenetic drugs, senolytic drugs, or anti-oxidants (eg. resveratrol).

U.S. Pat. No. 7,067,144 describes compositions and methods for inhibition of cartilage degradation. In some embodiments, these compositions and methods can be improved as described herein by combining them with bioadhesives for improved localization and retention.

In addition to the anti-cartilage degradation agent(s), the disclose compositions may include anti-pain and/or anti-inflammation agents. For example, the provided composition can further include one or more of classes of narcotic and non-narcotic analgesics (e.g., Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine). The provided composition can further include one or more of classes of anti-inflammatory agents (e.g., Alclofenac, Alclometasone Dipropionate, Algestone Acetonide, alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Decanoate, Deflazacort, Delatestryl, Depo-Testosterone, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Mesterolone, Methandrostenolone, Methenolone, Methenolone Acetate, Methylprednisolone Suleptanate, Momiflumate, Nabumetone, Nandrolone, Naproxen, Naproxen Sodium, Naproxol, Nimazone, Olsalazine Sodium, Orgotein, Orpanoxin, Oxandrolane, Oxaprozin, Oxyphenbutazone, Oxymetholone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Stanozolol, Sudoxicam, Sulindac, Suprofen, Talmetacin, Talniflumate, Talosalate, Tebufelone, Tenidap, Tenidap Sodium, Tenoxicam, Tesicam, Tesimide, Testosterone, Testosterone Blends, Tetrydamine, Tiopinac, Tixocortol Pivalate, Tolmetin, Tolmetin Sodium, Triclonide, Triflumidate, Zidometacin, Zomepirac Sodium).

In some embodiments improved drug targeting by the disclosed cartilage painting method decreases the dosing requirement for a given chondroprotective/chondroinductive drug compared to intra-articular injection. For example, the disclosed methods can comprise releasing 0.5-1.6 µg kartogenin (KGN) per 15-30 µg NPs over 3 weeks, in order to maintain approximately 10-25 µM KGN within the cartilage. This therapeutic dose of KGN is based on in vitro studies (10 µM KGN) and in vivo studies with untargeted systems (25-50 µM KGN). The NP dose is based on the NP retention levels in a cartilage volume comparable to that in the rat (20 mm$^3$).

The ratio of components can depend on the drug. In some embodiments, the method involves an agent:NP:CS-ald mass ratio of 0.03:1:12.5-0.2:1:12.5 (i.e. drug loading of NPs=2-12% w/w (including around 3-10%) and an NP:adhesive ratio of 1:12.5). Alternatively, NP:adhesive ratio could vary from 1:12.5-1:25.

Anti-Cancer Agents

Suitable anti-cancer agents include chemotherapeutic agents such as paclitaxel and doxorubicin, or biologic agents such as DNA (e.g. plasmid DNA for wild type p53), microRNAs, or peptides.

Example anti-cancer agents include: Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alkeran for Injection (Melphalan Hydrochloride), Alkeran Tablets (Melphalan), Alimta (Pemetrexed Disodium), Aloxi (Palonosetron Hydrochloride), Alunbrig (Brigatinib), Ambochlorin (Chlorambucil), Amboclorin (Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar (Irinotecan Hydrochloride), Capecitabine, CAPDX, Carac (Fluorouracil—Topical), Carboplatin, Carboplatin-Taxol, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, Chlorambucil-Prednisone, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Ethyol (Amifostine), Etopophos (Etoposide Phosphate), Etoposide, Etoposide Phosphate, Evacet (Doxorubicin Hydrochloride Liposome), Everolimus, Evista (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), Folfiri, Folfiri-Bevacizumab, Folfiri-Cetuximab, Folfirinox, Folfox, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, Gemcitabine-Cisplatin, Gemcitabine-Oxaliplatin, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituximab, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq (Atezolizumab), Temodar (Temozolomide), Temozolomide, Temsirolimus, Thalidomide, Thalomid (Thalidomide), Thioguanine, Thiotepa, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

Delivery Vehicle

The disclosed delivery system can involve nanoparticles that are limited in size from about 5 nanometers to about 750 nanometers in diameter, including about 10 to about 500 nanometers, about 20 to about 200 nanometers, and about 30 nanometers to about 100 nanometers.

Preferred particles are biodegradable structures that biodegrade and release loaded drug at therapeutic levels over a period of time preferably between from about 1 to about 150 days, preferably from about 7 to about 60 days, with from about 14 to about 30 days being more preferred.

It is understood by those in the art that drug release from nanoparticles may occur by a combination of physical processes, which include, but are not limited to, diffusion and degradation and may be described by complex kinetic processes that are unique to each carrier formulation and combination of anabolic and anti-catabolic therapeutic agents.

Preferred particles are biocompatible with targeted tissues of the joint and the local physiological environment into which the dosage form is administered, including yielding biocompatible biodegradation products. Suitable compositions include biodegradable particles formulated from natural polymers, including hyaluronan, chitosan, collagen, gelatin and alginate. These natural polymers may be combined with other polymers to produce copolymer particles composed of, for example, chitosan and gelatin. Synthetic biodegradable poly(alpha-hydroxy esters) such as polylactic acid (PLLA), polyglycolic acid (PGA) and the copolymer PLGA have been used successfully for the production of microparticles that incorporate protein therapeutics, such as human growth hormone. Another example of a biodegradable polymer that may be suitable for use in preparing particles are amphiphilic ABA triblock copolymers such as poly(ethylene oxide):poly(3-hydroxybutyrate):poly(ethylene oxide).

The polymers may be prepared from one or more of the following monomers: acrylic acid, or any ester thereof, such as methyl acrylate, ethyl acrylate, propyl acrylate, butyl acrylate, 2-ethyl hexyl acrylate or glycidyl acrylate; methacrylic acid, or any ester thereof, such as methyl methacrylate, ethyl methacrylate, propyl methacrylate, butyl methacrylate, lauryl mathacrylate, cetyl methacrylate, stearyl mathacrylate, ethylene glycol dimethacrylate, tetraethylene glycol dimethacrylate, glycidyl methacrylate or N,N-(methacryloxy hydroxy propyl)-(hydroxy alkyl) amino ethyl amidazolidinone; allyl esters such as allyl methacrylate; itaconic acid, or ester thereof; crotonic acid, or ester thereof; maleic acid, or ester thereof, such as dibutyl maleate, dioctyl maleate, dioctyl maleate or diethyl maleate; styrene, or substituted derivatives thereof such as ethyl styrene, butyl styrene or divinyl benzene; monomer units which include an amine functionality, such as dimethyl amino ethyl methacrylate or butyl amino ethyl methacrylate; monomer units which include an amide functionality, such as acrylamide or methacrylamide; vinyl-containing monomers such as vinyl ethers; vinyl thioethers; vinyl alcohols; vinyl ketones; vinyl halides, such as vinyl chlorides; vinyl esters, such as vinyl acetate or vinyl versatate; vinyl nitriles, such as acrylonitrile or methacrylonitrile; vinylidene halides, such as vinylidene chloride and vinylidene fluoride; tetrafluoroethylene; diene monomers, such as butadiene and isoprene; and allyl ethers, such as allyl glycidyl ether.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention can be characterized by a lactic acid:glycolic acid ratio of approximately 85:15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., the PLGA block copolymer or PLGA-PEG block copolymer), may be selected to optimize for various parameters such as water uptake, therapeutic agent release and/or polymer degradation kinetics can be optimized.

For some drug combinations, the optimal release kinetics may consist of a dual-release process, wherein each active agent demonstrates a different sustained release kinetic profile to provide the most optimal drug pharmacokinetics within the joint. Those skilled in the art will recognize, based on the disclosure herein, that the optimal release kinetics from the nanoparticles will vary for each individual drug, and will also be a function of the amount of drug loaded into particles during formulation, the size of the particles, and other physiochemical properties that are determined by the composition of the particles. Quantitative release rates for each drug from the encapsulating particles resident in the joint can be adjusted to obtain the optimal therapeutic concentration to achieve the desired therapeutic concentrations. In vitro studies can be conducted to characterize the dual-release kinetics for the sustained release formulation in which each component (e.g., the anabolic drug and the catabolic inhibitor) demonstrate sustained release over a period of 7-30 days, by way of example. Methods to quantitate the amount of each drug released into the synovial fluid are well known in the art, and may include measurements of radioactively labeled drug. Alternatively, it is possible to covalently attach fluorescent or other optical reporter molecules to prepare labeled drugs. Those skilled in the art will recognize that many indirect methods for quantitation exist, such as ELISAs or mass-spectrometry, which are specific to each agent.

BioAdhesive

The bioadhesive can be any natural or synthetic molecule capable of binding to cartilage in a joint. In some embodiments, the bioadhesive comprises a chondroitin sulfate, such as chondroitin sulfate aldehyde (CSAld). In some embodiments, the bioadhesive comprises aldehyde functionalized hyaluronic acid. In some embodiments, the bioadhesive comprises chitosan. In some embodiments, the bioadhesive comprises cellulose. In some embodiments, the bioadhesive comprises dextran. In some embodiments, the bioadhesive comprises poly(ethylene)glycol.

Methods

A method is disclosed herein for treating a cartilage-related condition in a subject that involves administering to a joint of the subject a first composition comprising a chondrogenic or chondroprotective agent contained within a delivery vehicle and a second composition comprising a bioadhesive in an effective amount of to adhere and seed the delivery vehicle to cartilage in the joint of the subject.

In some embodiments, the cartilage-related condition is a articular cartilage defect including rupture or detachment, a meniscal defect including a partial or complete tear, Osteoarthritis, Traumatic cartilage rupture or detachment, disease or damage to the meniscus and/or patella, Ankylosing spondylitis, Capsulitis, Psoriatic arthritis, Rheumatoid arthritis, Systemic lupus erythematosus, Juvenile idiopathic arthritis, or X-linked hypophosphatemic rickets.

In some embodiments, the cartilage-related condition is a rupture or detachment of the cartilage, a meniscal defect including a partial or complete tear or damage or a disease effecting the meniscus and/or patella. In some embodiments, a cartilage-related condition is selected from any or a combination of diseases from the following group: osteoarthritis (referred to herein as "OA" which results from breakdown of cartilage), including knee, finger, wrist, hip, ankle, elbow, toe, shoulder, and spinal osteoarthritis, traumatic cartilage rupture or detachment, ankylosing spondylitis, capsulitis, psoriatic arthritis, rheumatoid arthritis (RA), systemic lupus erythematosus, juvenile idiopathic arthritis, Chondropathy, Chondrosarcoma, Chondromalacia, Polychondritis, Relapsing Polychondritis, Slipped epiphysis, Osteochondritis Dissecans, Chondrodysplasia, Costochondritis, X-linked hypophosphatemic rickets, Osteochondroma, Chondrosarcoma (malignant), Osteoarthritis Susceptibility (types 1-6), Spondylosis, Osteochondroses, Primary chondrosarcoma, Chondrodysplasia, Tietze syndrome, Dermochondrocorneal dystrophy of Francois, Epiphyseal dysplasia, multiple, (types 1-5), Ossified Ear cartilages with Mental deficiency, Muscle Wasting and Bony Changes, Carpotarsal osteochondromatosis, Achondroplasia, Chondrocalcinosis (types 1-2), Genochondromatosis, Chondrodysplasia (disorder of sex development), Chondroma, Achondrogenesis (types 1A, 1B, 2, 3, 4, Langer-Saldino Type), Type II Achondrogenesis-Hypochondrogenesis, Atelosteogenesis, (type 1, 2 and III), Pyknoachondrogenesis, Pseudoachondroplasia, Osteoarthropathy of fingers, familial, Diastrophic dysplasia, Dyschondrosteosis-nephritis, Coloboma of Alar-nasal cartilages with telecanthus, Alar cartilages hypoplasia-coloboma-telecanthus, Pierre Robin syndrome-fetal chondrodysplasia, Dysspondyloenchondromatosis, Achondroplasia regional-dysplasia abdominal muscle, Osteochondritis Dissecans, Familial Articular Chondrocalcinosis, Tracheobronchomalacia, Chondritis, Dyschondrosteosis, Maffucci Syndrome, Jequier-Kozlowski-skeletal dysplasia, Chondrodystrophy, Cranio osteoarthropathy, Tietze's syndrome, Hip dysplasia-enchondromata-enchondromata, Bessel-Hagen disease, Chondromatosis (benign), Enchondromatosis (benign), chondrocalcinosis due to apatite crystal deposition, Meyenburg-Altherr-Uehlinger syndrome, Enchondromatosis-dwarfism-deafness, Astley-Kendall syndrome, Synovial osteochondromatosis, Chondrocalcinosis familial articular, Severe achondroplasia with developmental delay and acanthosis nigricans, Chondrocalcinosis, Keutel syndrome, Stanescu syndrome, Fibrochondrogenesis, Hypochondroplasia.

A subject amenable for the treatment with the disclosed method includes a subject who has one or more symptoms of a joint disorder or cartilage loss or damage, including one or more symptoms from the group of: joint swelling, joint pain, joint redness, joint laxity, mild arthritis symptoms, haemorrhagic joint effusion, inflammatory joint effusion, joint hypermobility, non-inflammatory joint effusion or other types.

Also disclosed is a method is disclosed herein for treating cancer a subject that involves administering to tumor margins of the subject a first composition comprising an anti-cancer agent contained within a delivery vehicle and a second composition comprising a bioadhesive in an effective amount of to adhere and seed the delivery vehicle to the tumor margins.

The cancer of the disclosed methods can be any solid tumor in a subject containing cells undergoing unregulated growth, invasion, or metastasis. Thus, the cancer can be a sarcoma, lymphoma, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, or testicular cancer.

Administration

The disclosed compositions can be painted onto tissues, such as cartilage surfaces or tumor margins, during surgical procedures. Therefore, the compositions may be perioperatively applied, e.g. during arthroscopic surgery of anatomic joints. As used herein, the term "perioperative" encompasses application intraprocedurally, pre- and intraprocedurally, intra- and postprocedurally, and pre-, intra- and postprocedurally. Preferably the compositions are applied postprocedurally. Arthroscopic techniques for which the present solution may be employed include, by way of non-limiting example, partial meniscectomies and ligament reconstructions in the knee, shoulder acromioplasties, rotator cuff debridements, elbow synovectomies, and wrist and ankle arthroscopies. The irrigation solution is continuously supplied intraoperatively to the joint at a flow rate sufficient to distend the joint capsule, to remove operative debris, and to enable unobstructed intra-articular visualization. The procedure can also be performed under gas arthroscopy or in an open joint procedure, e.g. after intra-articular fracture.

A number of embodiments of the invention have been described. Nevertheless, it will be understood that various modifications may be made without departing from the spirit and scope of the invention. Accordingly, other embodiments are within the scope of the following claims.

EXAMPLES

Example 1

A regenerative OA therapy must include the replacement of lost/dead cartilage cells with cells that can facilitate rebuilding of cartilage tissue. Exogenous cell delivery to joints is expensive and has generated highly variable clinical results, due to poor cell survival and engraftment. Spontaneous cartilage repair has been demonstrated in limited circumstances. In "super-healer" MRL/MpJ mice (Mak, J., et al. Scientific reports 6:23076 (2016)), MSCs migrate from within the joint to injured cartilage where they engraft. Indeed, MSCs reside in the synovial membrane, synovial fluid (SF), intra-articular fat pad, and bone marrow of the joint where they play a role in tissue homeostasis and could be harnessed for cartilage repair. Interestingly, surgical microfracture procedures have been used to recruit MSCs from bone marrow to cartilage to repair small, focal cartilage lesions in otherwise healthy joints. Biomaterials have been developed that augment the repair process induced by microfracture, which improves clinical outcomes and broaden its applicability (Sharma, B., et al. Science translational medicine 5:167ra166 (2013)). However, the presence of OA in the joint can confound cartilage tissue repair efforts because chronic inflammation and metabolic dysregulation impacts MSC migration and chondrogenesis. In addition, many chondrogenic growth factors and well-known stem cell recruiting factors have highly undesirable off-target effects in the joint, such as inducing bone overgrowth and synovial membrane thickening, which exacerbates pain and further joint deterioration. This underscores the needs for targeted delivery, as well as careful consideration of whole joint physiology in selecting recruiting agents to deliver to OA cartilage.

Figure 2:
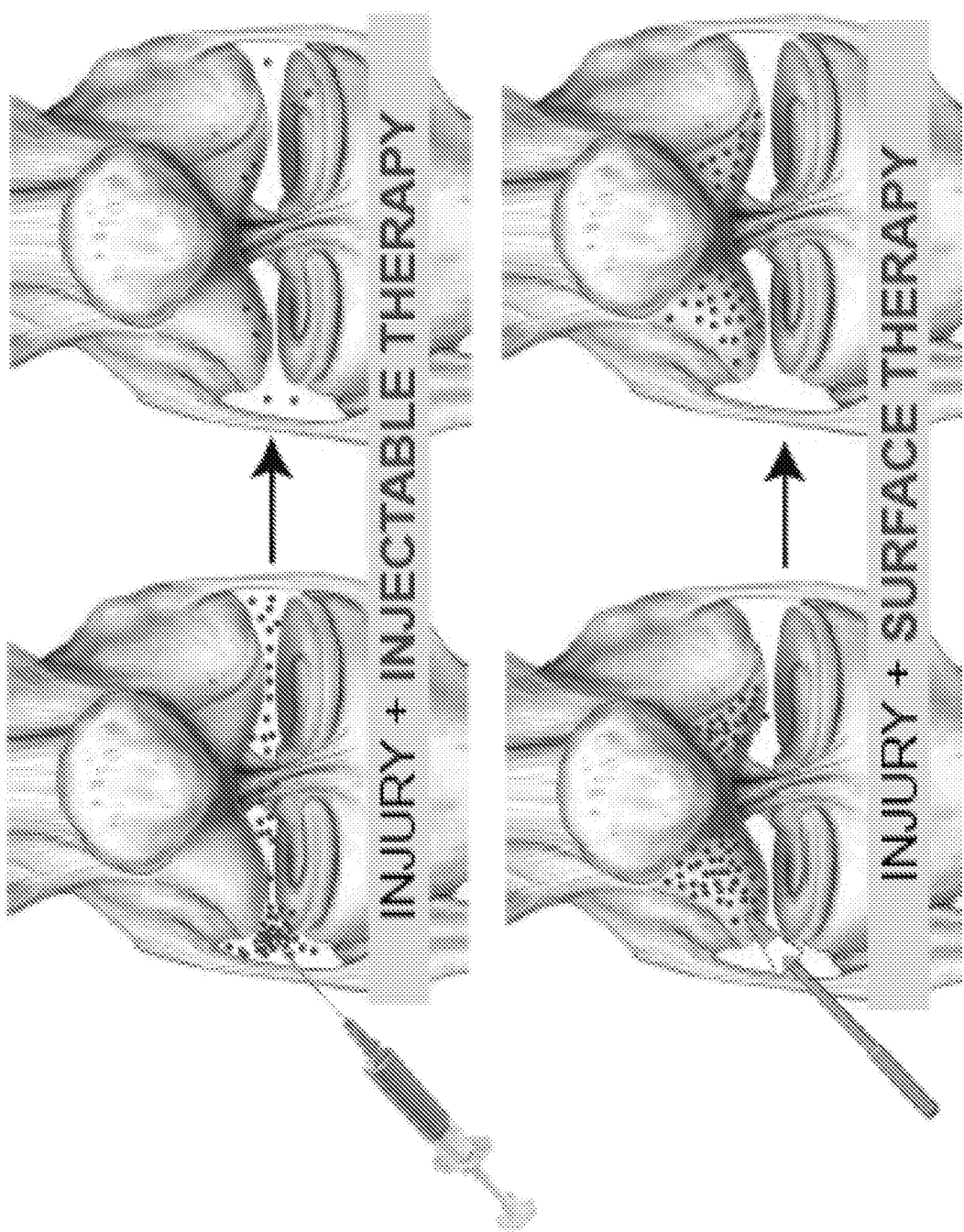
FIG. 2. Overview of NP delivery. We propose direct application and binding of NPs to the cartilage surface (bottom) to improve drug localization to cartilage compared to injection of NPs in the joint (top) in order to prevent or reserve OA after joint injury.
Figure 3A:
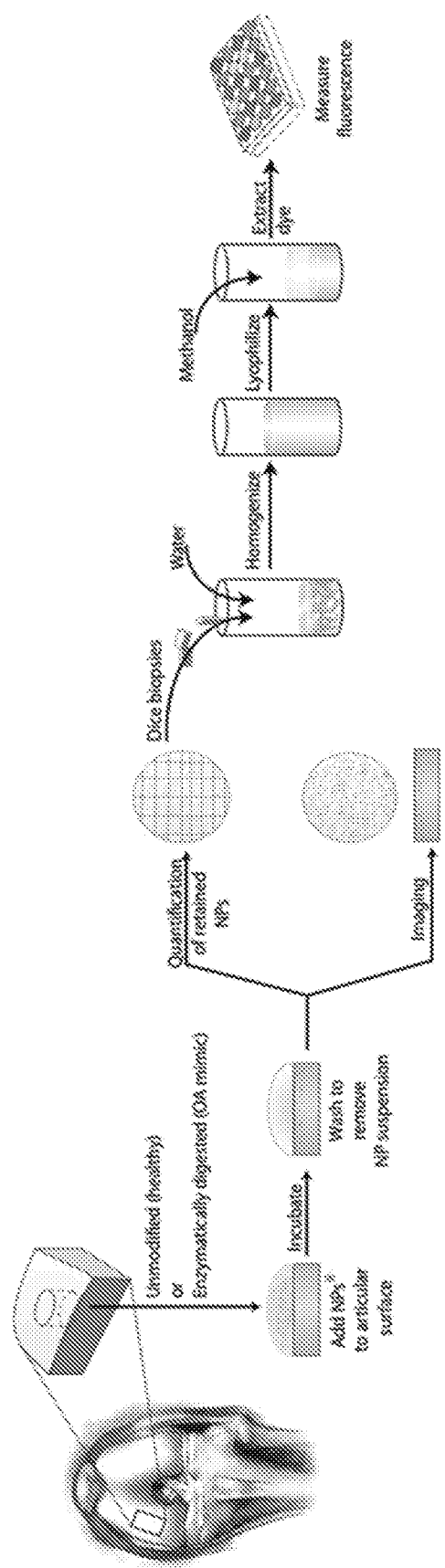
FIG. 3. NP-Cartilage Interactions. (A) Schematic of methods where healthy and "OA" bovine cartilage explants were treated with fluorescently labeled PLGA NPs [PVA-coated are anionic (−) and DMAB-coated are cationic (+)] with and without synovial fluid, followed by imaging, dye extraction, and fluorescent measurement of dye/NP concentration. (B) Quantification of the NP retention, n=3-6 per group. (C) Histology illustrates proteoglycan depletion in enzymatically digested "OA" tissue (right) compared to healthy tissue (left). (D) Fluorescence microscopy observations consistent with quantitative data. Bar=100 microns.
Figure 3B:
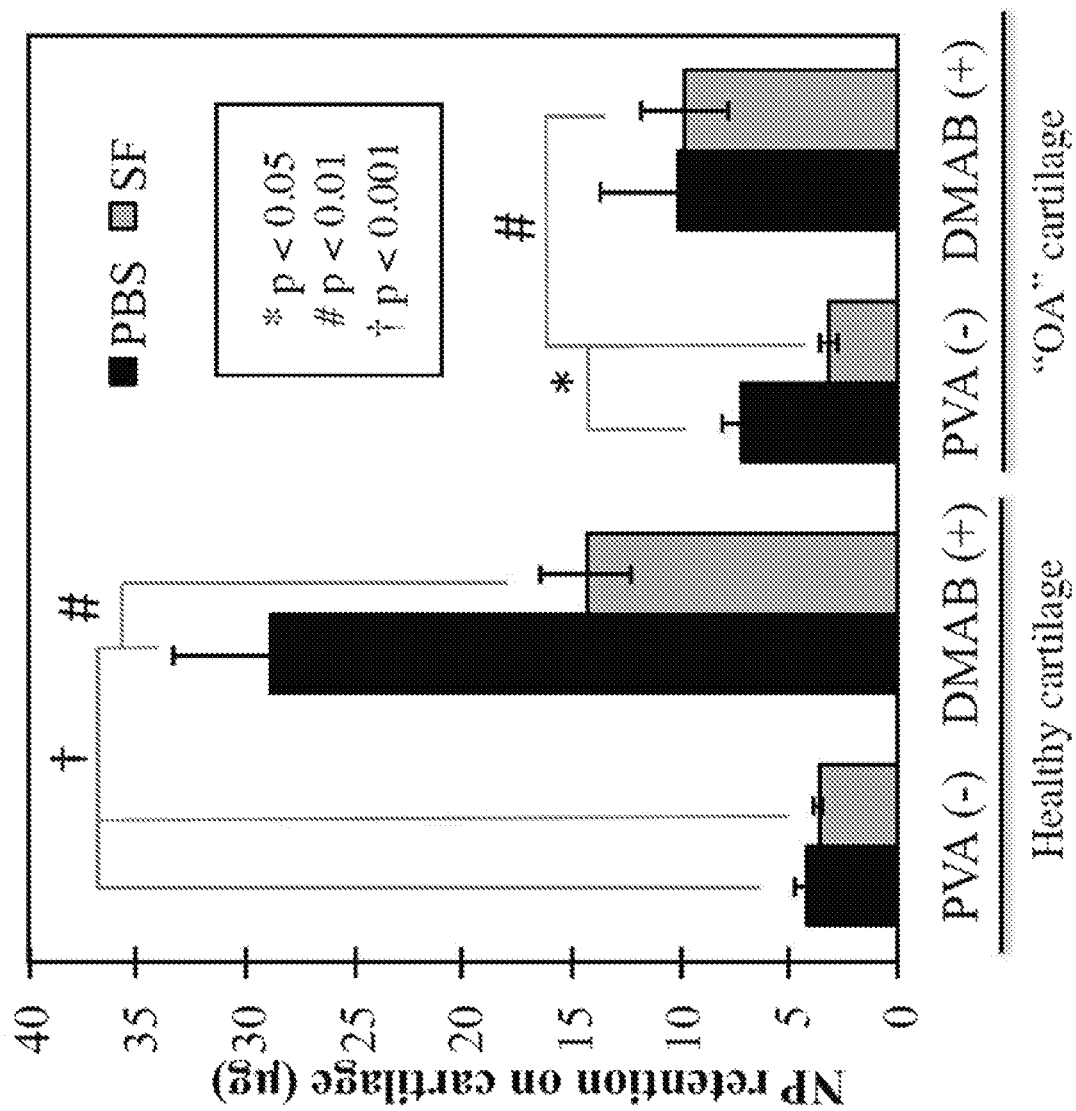
Figure 3C:
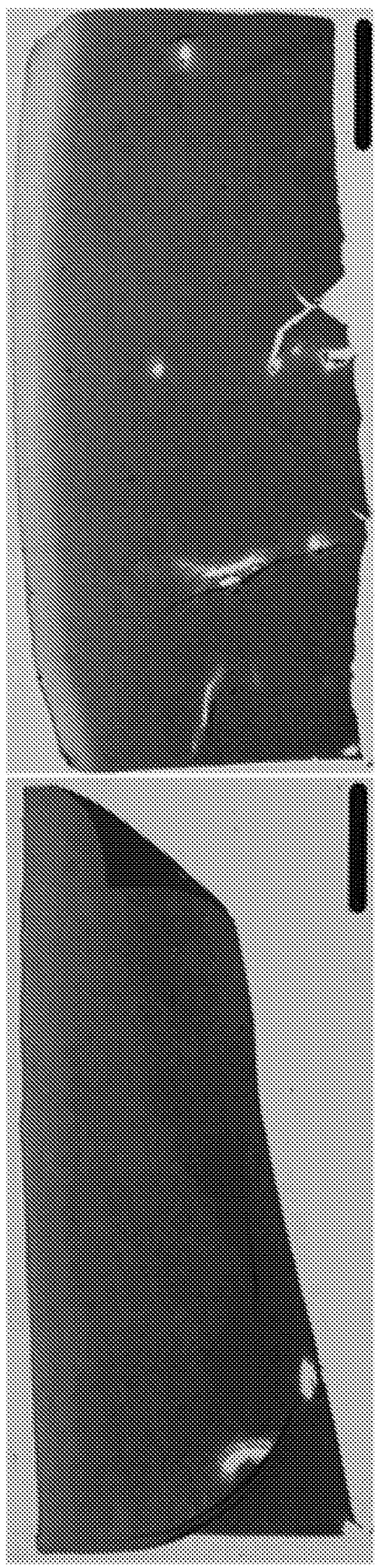
Figure 3D:
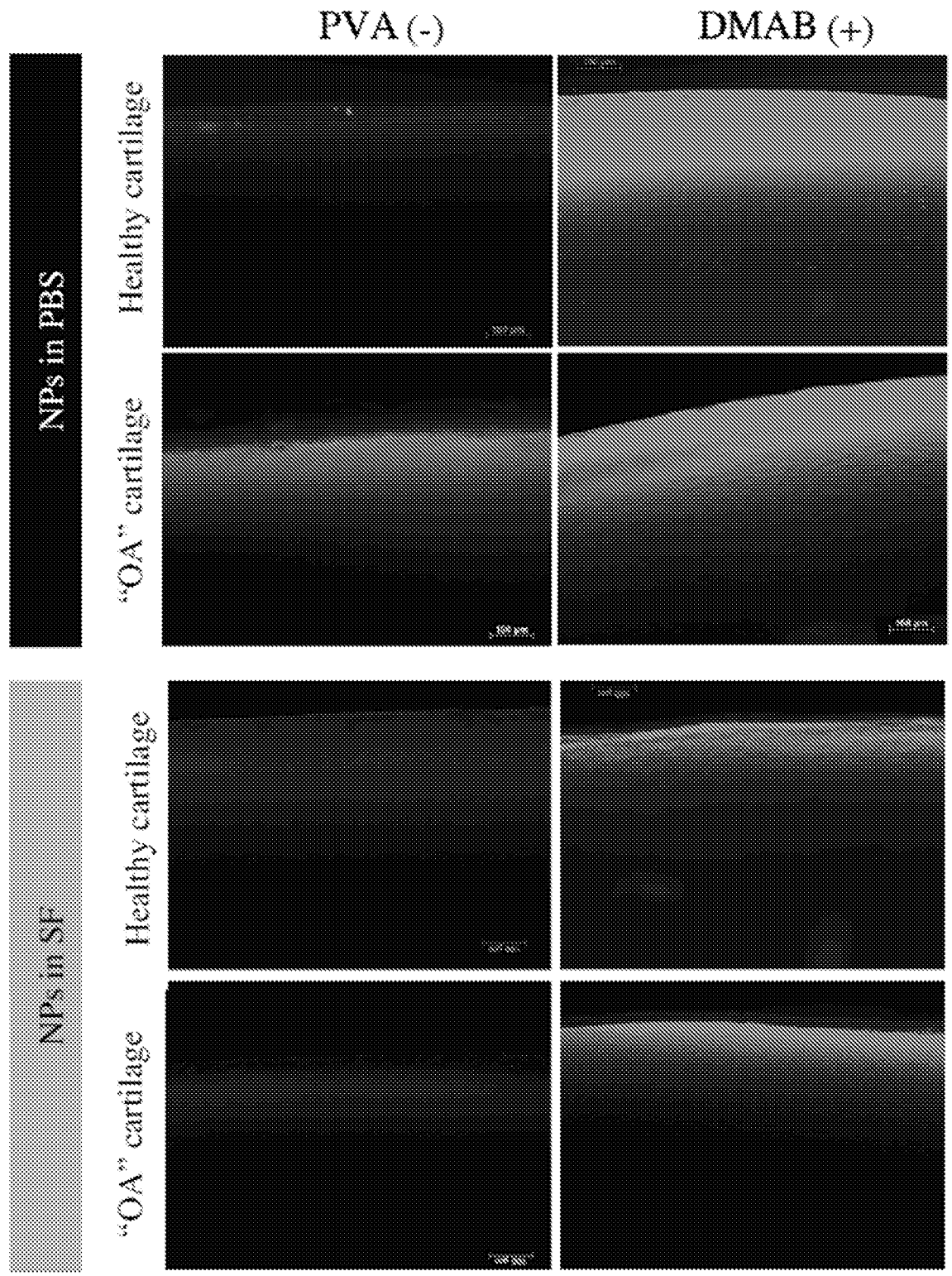

This example explores a new NP delivery approach that addresses the existing hurdles in successful drug localization to cartilage and answers a key question in the field—does targeted delivery in the joint improve efficacy of disease-modifying OA drugs? This example focuses on a form of OA known as post-traumatic OA (PTOA), which is degenerative joint disease initiated by a joint injury. Common joint trauma, such as an anterior cruciate ligament rupture or meniscal tears, initiates a cascade of events that ultimately lead to inflammation, chondrocyte death, and proteoglycan (PG) loss from the cartilage ECM. Though PG loss alone may be potentially reversible, more than half of these patients develop OA 10-15 years later even if they received surgery to stabilize the joint. Because joint injuries are common in young, athletic, and military populations, the onset of PTOA is particularly devastating as these patients lose joint function and require joint replacements earlier in life. PTOA presents an opportunity for early intervention in a high-risk patient population and is a good test-bed for new OA therapeutics. To bypass the inefficiencies related to cartilage targeting after injection, an NP system is disclosed that can be directly applied or "painted" onto the cartilage surface when the joint is accessed surgically (FIG. 2). Surgical access or arthroscopy is often conducted to debride damaged tissue and/or stablilize the joint after injury, thereby posing an opportunity to localize chondroinductive agents to the entire cartilage surface. The central hypothesis of this example was that enhanced targeting and retention of chondroinductive agents into cartilage would improve their efficacy and slow or reverse the progression of OA (FIG. 1). In order to test this hypothesis an NP system for site-specific retention in cartilage was engineered. The NP system was then be used to study and promote chondroinduction, defined as migration and chondrogenic differentiation of MSCs, in OA cartilage.

Studies were conducted to determine on how fundamental NP properties such as size, charge, and surface chemistry affect interactions with synovial fluid (SF), healthy cartilage, and enzymatically digested cartilage to mimic the PG depletion and permeability of OA cartilage (FIG. 3). First, there was a greater cartilage retention of cationic NPs ("DMAB") versus anionic NPs ("PVA"). However, cationic NP retention was reduced 2-fold in the presence of synovial fluid and 3-fold in OA explants (FIG. 3B). Synovial fluid contains proteins and polysaccharides that adsorb to the NPs and alter their properties. The cationic NPs experienced a reversal in surface charge in synovial fluid, which may have blocked electrostatic interactions with healthy cartilage. The loss of PGs in the OA tissue likely contributed to the reduction in cartilage retention of the cationic NPs. We had expected that the increased permeability of OA cartilage would facilitate NP penetration, but this was only observed in anionic NPs in saline. These data suggest that increased tissue permeability may facilitate NP entry, however NPs must minimize interactions with synovial fluid and sufficiently bind to the cartilage ECM upon tissue penetration in order to be retained. NPs functionalized to bind to the collagen network, which is more stable (i.e. little/no turnover) compared to PGs, were examined to determine how targeting modality and disease state of cartilage affect NP retention. These studies also inspired the idea of direct application of NPs to the cartilage surface, as a way to minimize NP loss due to NP-synovial fluid interactions.

Figure 4:
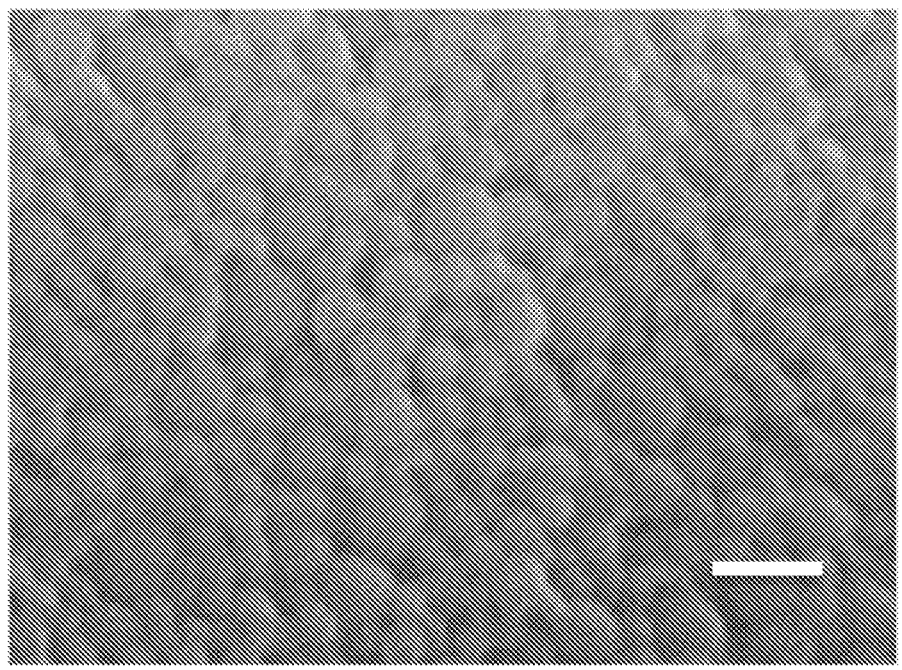
FIG. 4. SEM of PLGA-b-PEG NPs, ave diameter of 80 nm (bar=200 nm).

The goal was to achieve high NP retention in the extracellular space, in order to provide interstitial release of stem cell recruiting agents. The space between collagen cross-links in healthy cartilage has been estimated at 90 nm, and NPs smaller than 30 nm have demonstrated uptake in chondrocytes. Therefore NPs in the 50-90 nm size range (FIG. 4), as well as in the 150-250 nm range (as in preliminary studies), are investigated to determine if the optimal NP size changes as degeneration (i.e. tissue permeability) progresses. NPs with tunable properties based on block copolymers of poly(lactic-co-glycolic acid) and poly(ethylene oxide) (PLGA-b-PEG) are synthesized by nanoprecipitation techniques to form NPs in the specified size ranges. Three different surface functionalization strategies are used to provide different cartilage binding mechanisms, including: 1) PLGA-b-PEG functionalized with cationic dodecyltrimethylammonium bromide (DMAB) to provide electrostatic interactions with GAGs as was done in preliminary studies, 2) PLGA-b-PEG functionalized with a collagen type II binding peptide (WYRGRLK (SEQ ID NO:1) (Rothenfluh, D. A., et al. Nature materials 7:248-254 (2008))) to provide specific binding to the collagen matrix of cartilage, and 3) PLGA-b-PEG functionalized with aldehyde groups to provide rapid, covalent (though non-specific) binding to the cartilage tissue on application (Wang, D. A., et al. Nature materials 6:385-392 (2007)). Synthesis of all PLGA-b-PEG polymers is be confirmed by 1H NMR. NPs are characterized for size and morphology (dynamic light scattering (DLS) and transmission electron microscopy TEM), zeta potential (Zeta Potential Analyzer), and surface functionalization (Fourier Transform Infrared Spectroscopy). Aldehyde substitution is also quantified by a hydroxylamine hydrochloride titration method.

Figure 5:
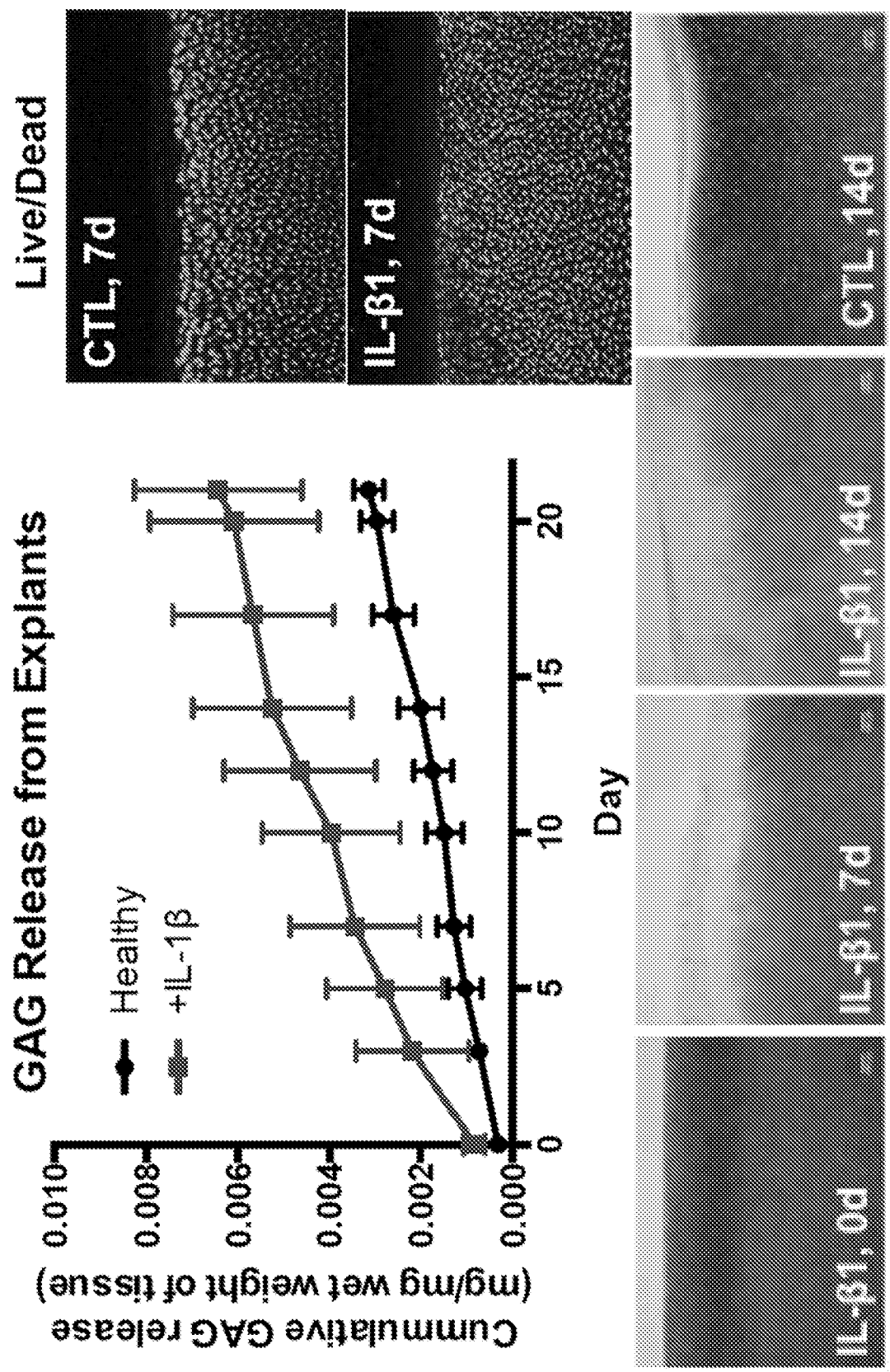
FIG. 5. Cytokine challenge explant model of OA. Cartilage explants cultured with IL-1β experience progressive GAG release by DMMB assay (graph above) and Safranin-O staining (histology, below), and cell death (Live/Dead, upper right). CTL indicates control culture with no IL-1β.

The NP formulations are evaluated for adhesion and long-term retention within cartilage explants. To create "OA" cartilage, rather than the enzymatic digestion used in preliminary studies, a cytokine challenge model is used to better mimic the biological process of OA and provide a basis for chondroinduction studies. Specifically, explants are treated with interleukin-1β (10 ng/mL) for 7 and 14 days, to represent two different stages of degeneration marked by glycosaminoglycan (GAG) release and chondrocyte death (FIG. 5). The explant surfaces are treated with fluorescently labeled NPs and evaluated for NP adhesion and depth of penetration via fluorescence microscopy after 5 and 15 minutes. Quantification of NP retention is done by high performance liquid chromatography (HPLC), after homogenization and dye extraction from the explants. To evaluate long-term retention and cytocompatibility, NP-treated explants are cultured for an additional two weeks and evaluated for NP content, cell viability (Live/Dead staining), and GAG release, compared to control explants with no NPs. If cytotoxicity is observed in any of the formulations, lower doses or degrees of substitution (eg. aldehyde substitution or DMAB concentration) are examined.

Figure 6A:
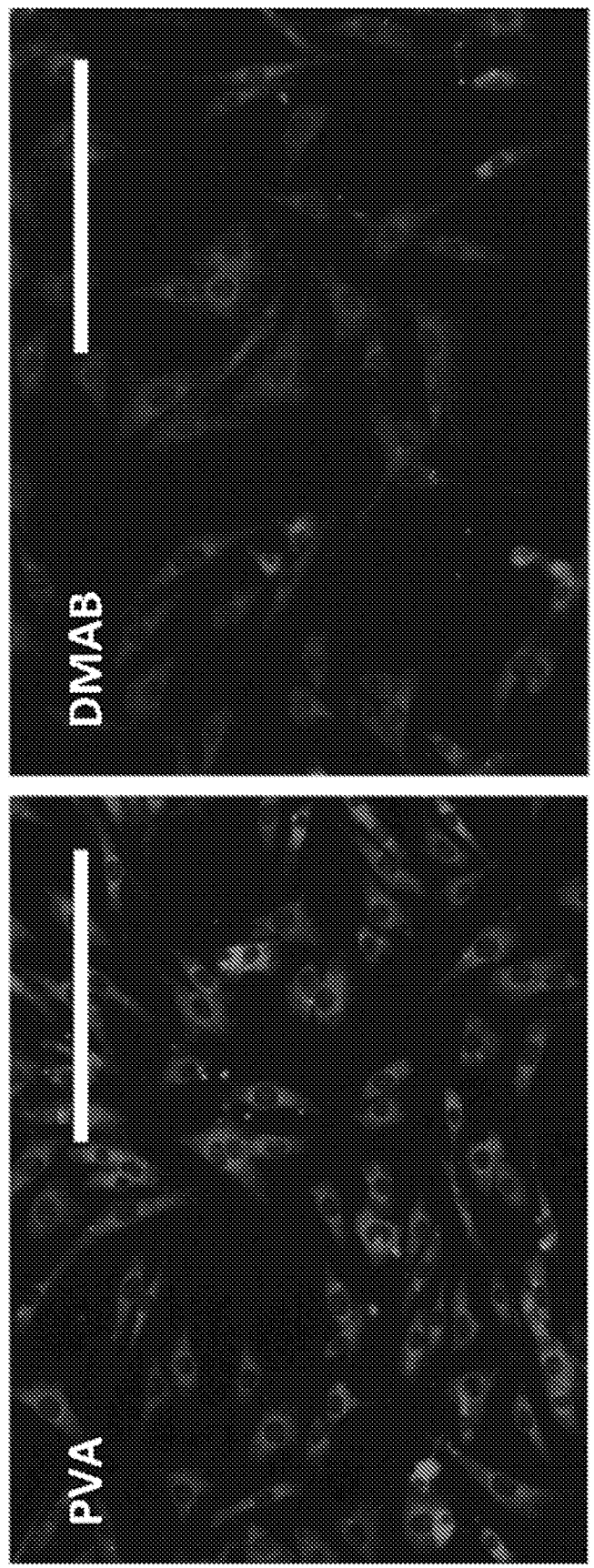
FIG. 6. Synoviocyte uptake of NPs (A) imaged after a single wash with fluorescence microscopy (0% synovial fluid, six hour incubation) and (B) quantified by HPLC on extracts from cell lysis after four washes (n=6). Fluorescence normalized to DNA content determined via Pico Green assay. (α) $p<0.05$, (β) $p<0.01$ for an individual treatment condition relative to 0% synovial fluid via Dunnett's tests. Scale bar=200 μm. Note that the fluorescence intensity between micrographs of PVA and DMAB NPs cannot be directly compared due to differences in dye loading efficiencies of the two formulations. NP quantification, however, was done using independent standard curves to account for these differences.
Figure 6B:
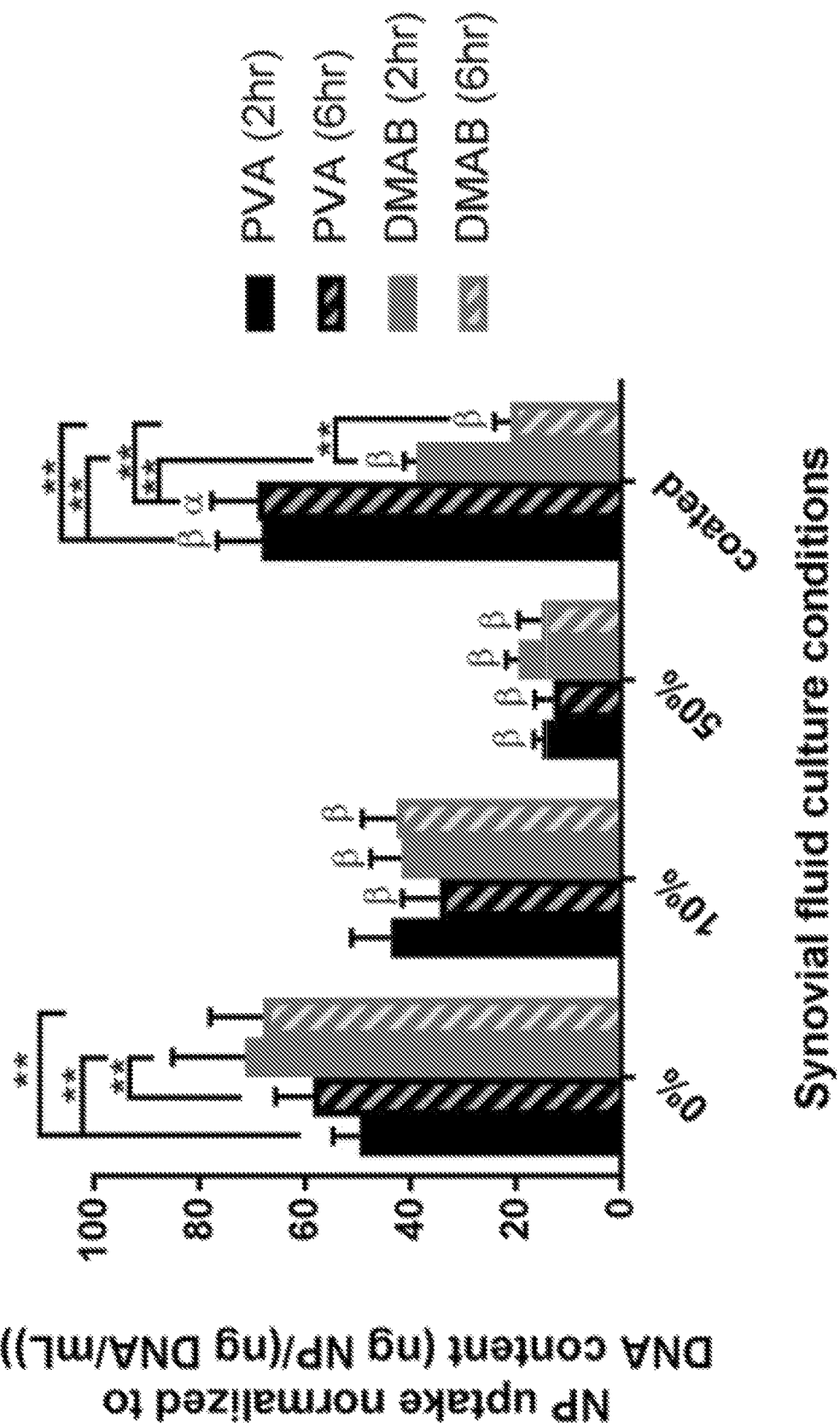

NP formulations that demonstrate high retention and cytocompatibility are used to develop a painting method. To determine an acceptable method, the consistency and level of NP retention after application with a surgical sponge and with or without a chondroitin sulfate (CS)-based tissue sealant are quantified on explants and cadaveric rat joints. The CS is functionalized with aldehyde groups (CSald), which rapidly bind to the amines on the collagen network. In preliminary studies, the addition of the CS-ald to the NP application resulted in visibly higher levels of cartilage retention compared to the NPs alone (FIG. 6). NP content and cell viability over time in explants is measured.

NP binding to the collagen matrix, via the binding peptide or covalent bonding, is expected to more effective for cartilage retention than electrostatic NP-cartilage interaction, particularly when GAG depletion has occurred. NP selection is based on high cartilage retention at cytocompatible levels either with or without the CS-ald sealant. If the CS-ald sealant alone demonstrates benefits to cartilage health (i.e. reduced GAG loss or improved cytocompatibility), then it is carried forward into the next phase of experiments, and included in "vehicle control" groups.

Figure 7:
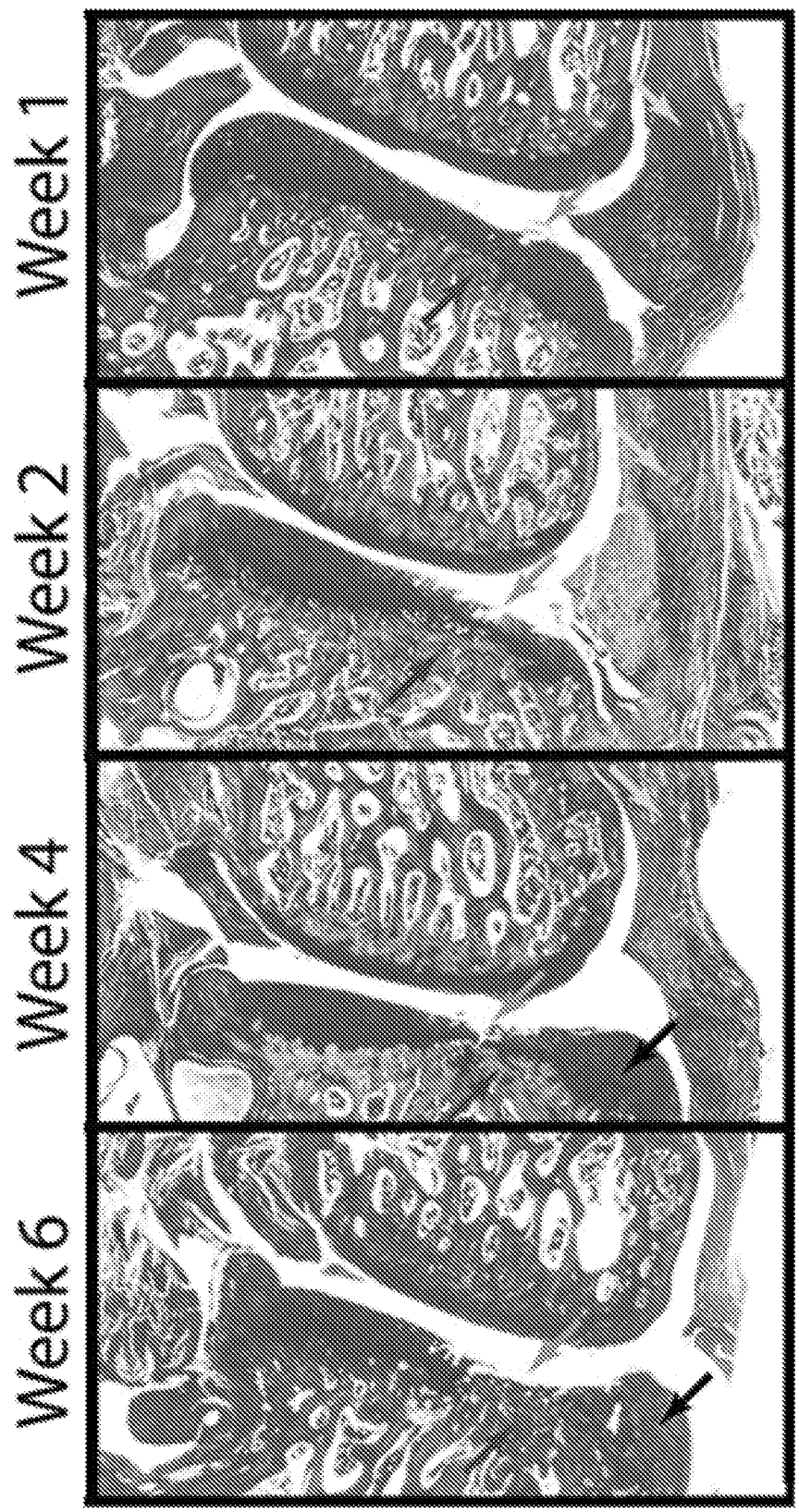
FIG. 7. Representative histology MMT. Arrows denote the following: cartilage lesion or proteoglycan loss (orange), ossification/calcified cartilage damage (red), synovitis (yellow), subchondral bone microfracture/edema (green), and osteophytes formation (black).
Figure 8:
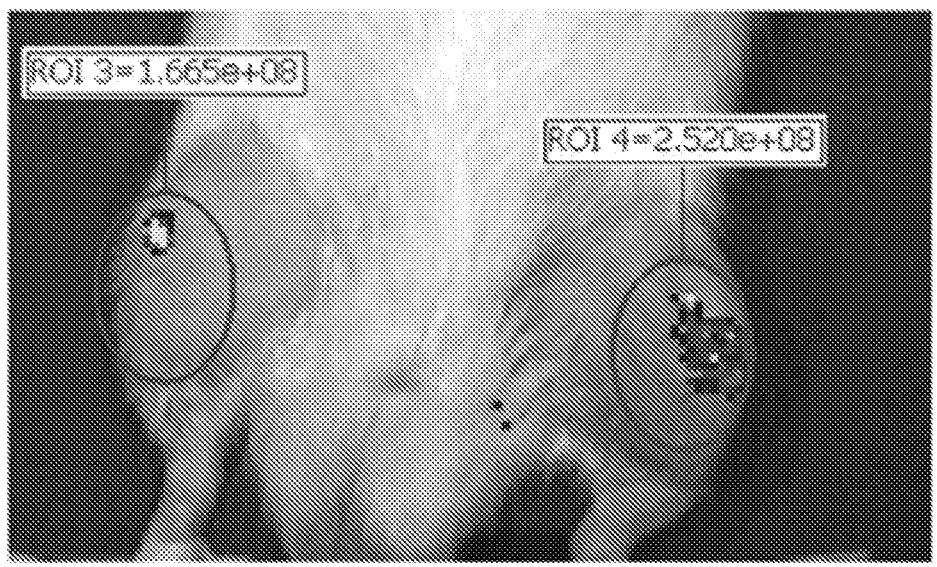
FIG. 8. IVIS imaging of NIR dye-loaded NPs in cadveric rat joint.
Figure 9A:
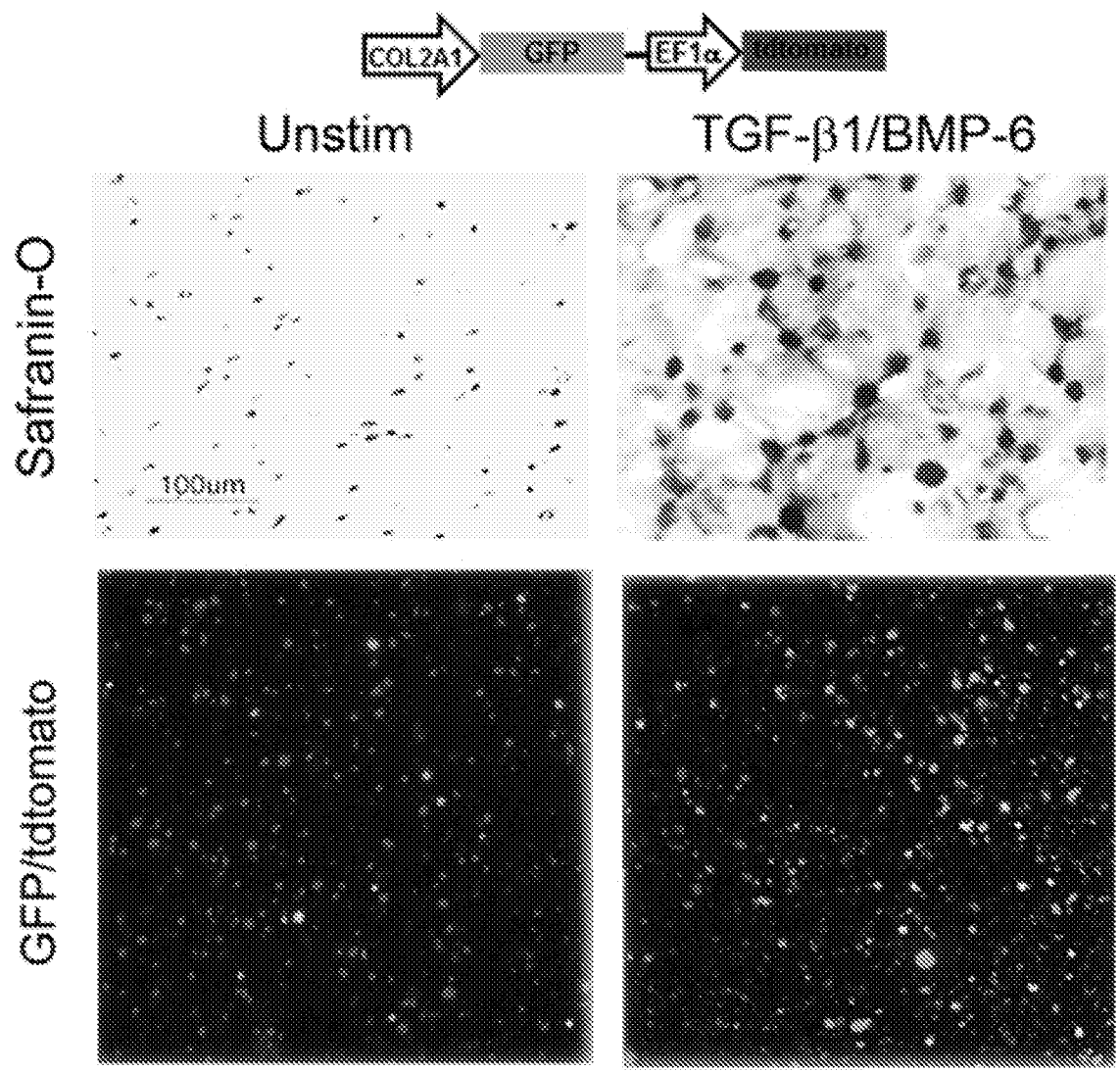
FIG. 9. MSC transduction with lentiviral vectors containing chondrocyte-specific transcriptional reporters. Expression of reporters (GFP and luciferase) correspond to GAG production (A, top) and chondorgenic gene expression (C).
Figure 9B:
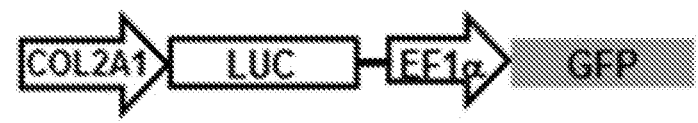
Figure 9B:
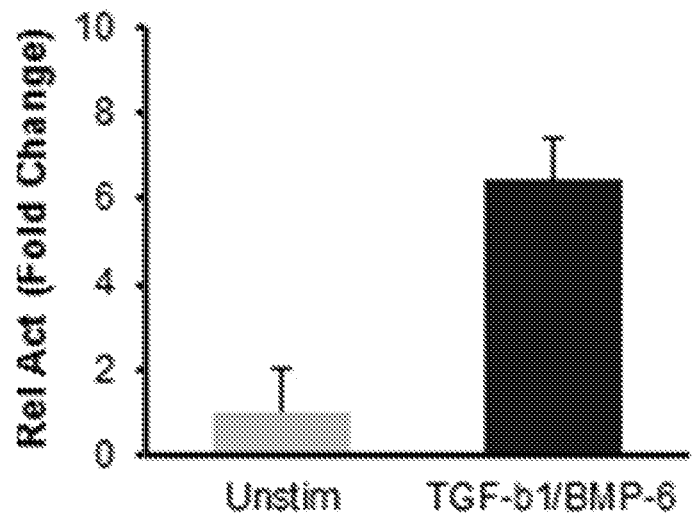
Figure 9C:
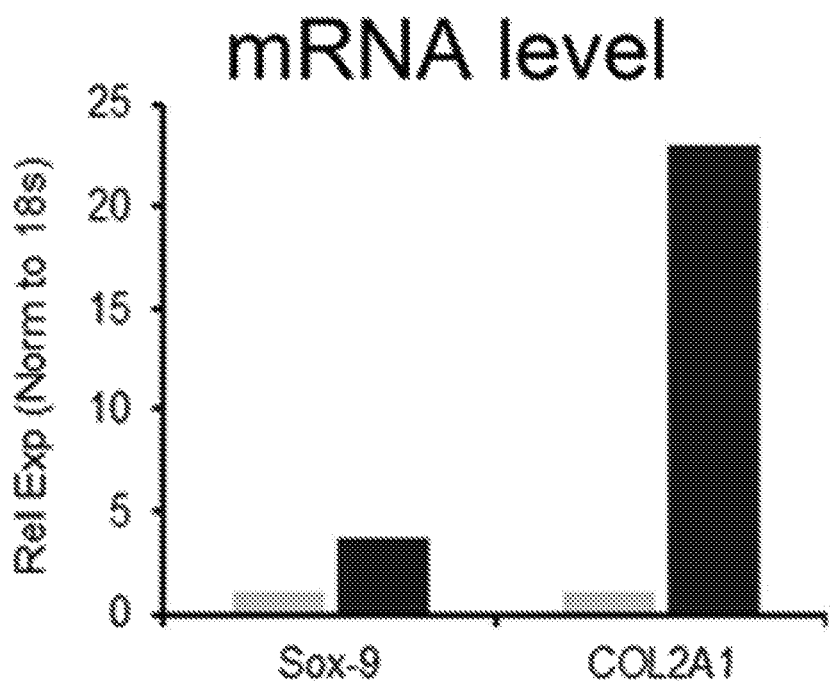

In vivo biodistribution studies are conducted to compare NP painting with intra-articular injection of cartilage-targeted NPs in healthy and OA joints. Four NP formulations are selected from ex vivo studies: the NP formulation with highest early OA cartilage retention, highest OA cartilage retention compared to healthy, highest healthy cartilage retention, and an untargeted NP control. All animal studies are conducted in accordance to the UF Institutional Animal Care and Use Committee guidelines. A well-established rodent model of OA that surgically simulates a medial meniscus tear (MMT), a common precursor to human OA, is used. MMTs result in a well-known cascade of degenerative changes over 4-6 weeks (FIG. 7) that emulates many of the pathological features of clinical OA. In this study, a cohort of Sprague-Dawley rats (n>3 mo old, n=6/group) receive either a surface treatment or injection with infrared-dye (SDB5491) labeled-NPs at the time of MMT surgery prior to degenerative changes. Another cohort of rats are treated 7-10 days after MMT surgery, which coincides with early stage OA when surface defibrillation and PG loss in cartilage occurs but precedes the development of large, full thickness lesions that develop in later stage OA. NP retention in the joint is evaluated over time using a Perkin Elmer IVIS in vivo imaging system. Joints will be imaged 2-3 times per week for 6 weeks, to semi-quantify the intensity and duration of fluorescence signal in the joint after intra-articular administration for the different NP formulations (FIG. 8). NP biodistribution within the joint is evaluated shortly after intraarticular injection at a time point, based on retention studies, where signal is relatively stable. Animals are sacrificed, the joint tissues (cartilage, synovial fluid, synovium, meniscus, ligaments, fat pad) dissected and imaged ex vivo, then quantified by HPLC to determine the percentage of NPs that localized to the different joint tissues under OA and normal conditions. Histological analysis (n=3 animals) is performed to assess the spatial distribution of NPs in the cartilage tissue and to confirm no adverse effects of NPs on the cartilage (compared to saline controls).

Identify Chondroinductive Agents for Regional Stem Cells Under OA Conditions

Inflammatory cytokines impact stem cell migration and differentiation across tissues. IL-1β, a predominant pro-inflammatory cytokine in OA, has been shown to inhibit MSC chondrogenesis. The impact of IL-1β, and inflammation in general, on stem cell homing is less clear, as inflammatory signals are responsible for mobilizing MSCs, however persistence or high levels of inflammatory cytokines may also inhibit MSC migration (Joos, H., et al. Arthritis research & therapy 15:R119 (2013)). The following studies seek to address the following question: how does the OA disease environment affect migration and chondrogenesis of the stem cell populations in the joint? MSCs from different sources have shown differences in proliferation, differentiation, and migration in standard conditions. Studies are needed that compare migration and chondrogenesis of different MSCs sources under inflammatory and OA conditions, to better guide the development of stem cell based therapies.

MSCs from rat and horse bone marrow, adipose tissue, and synovium are isolated to represent the endogenous stem cell populations in the joint in a species relevant to a small and large animal models of OA. Validation of the MSC populations is done via cell surface marker characterization (CD34–/CD105+) and standard multipotency assays. In order to quantify stem cell recruitment in a non-destructive, longitudinal manner, MSCs are transduced with lentiviral vectors that contain chondrocyte-specific transcriptional reporter systems. Vectors include a) Col2-Luc/EF1-GFP, which encodes for metridia luciferase (a secreted bioluminescent protein) under transcriptional control of the chondrocyte-specific COL2A1 promoter and green red fluorescent protein under constitutive control of the EF-1α promoter, and b) Col2-GFP/EF1-tdtomato, which encodes for green fluorescent protein (GFP) under transcriptional control of the COL2A1 promoter and constitutively expresses tdtomato. These vectors have been used to study and compare stem cell chondrogenesis in hydrogel-based scaffolds, where reporter expression was shown to be consistent with conventional methods for assessing chondrogenesis (FIG. 9).

Figure 10:
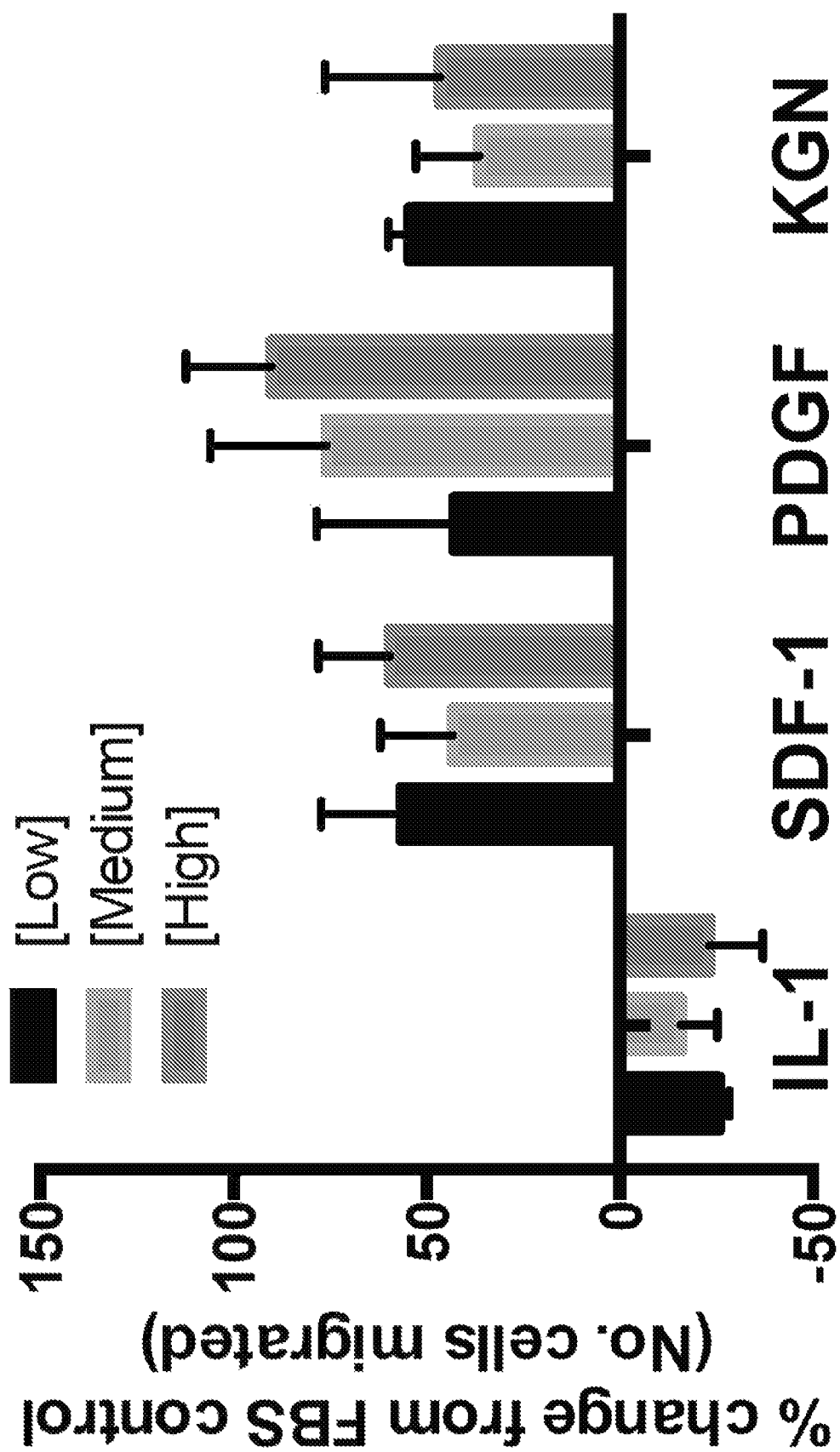
FIG. 10. MSC migration in response to different agents at different concentrations.

To determine if there are inherent differences in the migratory activity of the different MSC populations, migration in response to serum is first evaluated using 96-well Boyden chamber plates. To simulate OA conditions, MSC migration is evaluated in response to IL-1β (10 ng/mL and 50 ng/mL), conditioned medium from the established OA cartilage explants, and conditioned medium from normal explants. Results from each group are compared with a positive control of media with 10% serum to determine if the experimental conditions increase or decrease migration of MSCs. Preliminary data suggests that IL-1β may indeed inhibit migration of MSCs isolated from the fat pad of the joint (FIG. 10).

The response of MSCs to chondroinductive agents is evaluated, specifically platelet-derived growth factor (PDGF-BB) and kartogenin (KGN), which were selected based on their pleiotropic effects on promoting both migration and chondrogenesis of MSCs without adverse effects in the OA joint. PDGF-BB exerts chemotactic effects on bone marrow-derived MSCs, and facilitates new cartilage formation in the presence of IL-1β (Montaseri, A., et al. PloS one 6:e28663 (2011)). KGN is a recently discovered small molecule that has demonstrated promising chondrogenic and chondroprotective effects (Johnson, K., et al. Science 336:717-721 (2012)). KGN induces chondrogenesis by regulating the CBFβ-RUNX1 transcriptional program, and has demonstrated induction of SMAD 2/3 phosphorylation and lubricin/Prg4 expression, in a manner similar to chondrogenic growth factor TGFβ1. Kartogenin has been implicated in stimulating MSC recruitment in vivo, however, there are no reported migration studies with KGN, and therefore, the underlying mechanism for KGN-mediated recruitment is largely unknown. Stromal derived growth factor-one (SDF-1), a well-recognized chemotactic factor for stem cells, and will serve as a positive control in migration studies. However, SDF-1 has recently been shown to exacerbate OA pathogenesis (Li, P., et al. Mol Med Rep. 14(2):1475-82 (2016)) and therefore is not a viable candidate for future therapeutic development. Preliminary studies (FIG. 10) demonstrated migration of fat pad-derived MSCs in response to these agents. Migration across MSC sources in response to these agents under normal and OA conditions is further studied.

To evaluate chondrogenesis in normal vs OA conditions, Col2-Luc/EF1-GFP transduced MSCs from the different sources are used to created micromass cultures in a 96 well plate, and cultured in base media (unstimulated), standard chondrogenic induction media (TGF-β3), induction media plus IL-1β, OA conditioned media plus TGF-β3, and normal cartilage conditioned media plus TGF-β3. Medium is assayed twice weekly over 3 weeks for bioluminescence, as a metric of chondrogenesis. To test the chondroinductive agents, chodnrogenesis of Col2-Luc/EF1-GFP transduced MSC micromass cultures are evaluated in base media, OA conditioned medium, normal conditioned medium, and IL-1β medium, with and without KGN and PDGFBB.

The studies provide new insights into the migratory and chondrogenic activity of MSCs isolated from different tissues within the joint under normal and OA conditions. The chondroinductive agent that is able to most effectively stimulate migration and chondrogenesis in OA conditioned medium is selected for NP-based delivery into cartilage. Since synovium-derived MSCs are the most accessible during early stage OA, the primary outcome for this example is a chondroinductive agent that demonstrates migration and chondrogenesis in this group. If one agent performs better for migration and the other for chondrogenesis, the agent that demonstrates superior performance in migration assays is selected for the purposes of this example—one that attracts stem cells and one that promotes chondrogenesis.

Testing Chondroinductive NPs for Slowing or Reversing OA Progression Ex Vivo and In Vivo Chondroinduction of stem cells in OA cartilage can protect the cartilage from degeneration and possibly rebuild lost tissue. MSCs can serve multiple roles in regenerative medicine—they can directly contribute to new tissue formation through engraftment and differentiation, and/or they can secrete factors that reduce the production of inflammatory cytokines and protect resident cells from apoptosis. Delineating these mechanisms is important to the progress of stem cell-based therapies, but a challenge, due to limitation in methods for tracking MSC fate. Here, the conditionally active reporters are used to independently quantify stem cell migration and chondrogenic differentiation, and elucidate the contribution of these processes to regenerating OA cartilage.

NPs that demonstrate the greatest localization to OA cartilage are loaded with the chondroinduction (CI) agent to create CI-NPs. Loading, size and zeta potential of the NPs are evaluated. Release profile from the NPs is determined in saline, synovial fluid, and within cartilage explants. Integrity and bioactivity of the agent released from the NPs are confirmed by HPLC (for KGN) or ELISA (for PDGF), respectively, as well as by stem cell migration and chondrogenesis assays. Preliminary KGN-loaded NPs stimulated MSC chondrogenesis at levels comparable to TGF-β3, a potent chondrogenic growth factor.

NP-mediated chondroinduction of MSCs is evaluated in an ex vivo. OA cartilage explants will be treated with CI-NPs followed by addition of Col2-GFP/EF1-tdtomato MSCs. Explants are evaluated non-destructively over time by confocal microscopy for stem cell migration into the explant and chondrogenic differentiation (FIG. 12), which is quantified for ratio of red to green/yellow cells in Image J. At the end of the culture period (~3 wks), explants are digested and evaluated by flow cytometry for percentage of MSCs that are chondrogenic (i.e. labeled red and green vs. red only). Control groups include bolus delivery of the recruiting agent, control unloaded NPs, untreated controls (no NPs). In addition, explants treated with loaded NPs but no MSCs are evaluated to determine the effects of the agent alone. Cartilage protection or regeneration is evaluated by GAG release into the medium, expression of catabolic (MMP, aggrecanase), anabolic (collagen II, aggrecan), and inflammatory genes (IL-1, IL-6), and production of pro- and anti-inflammatory cytokines (Qiagen ELISArray Cytokine and Chemokine Kit). The CINPs can increase stem cell migration and chondrogenesis in OA explants, which slow or reverse the OA progression, determined by a reduction in GAG loss, decreased expression of catabolic genes, increased expression of anabolic genes, and decrease gene and protein expression of inflammatory cytokines. The quantitative assessments for stem cell presence and chondrogenic differentiation provide new insights into whether extent of overall migration or extent of chondrogenesis contributes most to chondroprotection.

The CI-NP system is tested in vivo for its ability to slow OA progression. CI-NPs are administered in one cohort of rats at the time of MMT and in another cohort at 7-10 days after MMT, and evaluated 3 and 6 weeks later. Control groups include cartilage painting with free CI agent and vehicle controls, injection of free CI agent and CI-NPs, and injection with vehicle controls. Outcome measures are histology (Osteoarthritis Research Society International scoring system), behavioral analysis (pain and gait), and synovial fluid analysis for biomarkers of catabolism (CTX II) and inflammation (MCP-1) by ELISA. In addition to gait, mechanosensitivity as a metric of pain in rodents is measured by a paw withdrawal threshold technique. These studies provide insights into how treatment at time of injury vs. after degeneration impacts multiple therapeutic outcomes. Histology is the primary outcome for preclinical assessments of OA, and in this case CI-NPs can improve OARSI scores by 50% compared, to compare with studies that use repeat injections of OA drugs. Coincidentally, if joint structures are preserved, there can be a decrease in CTX-II and MCP-1 levels, and a decrease in pain.

Example 2

Post-traumatic OA (PTOA) is a form of OA that is attributable to specific joint injury/trauma. PTOA comprises 12% of the OA patient population3 and is especially prevalent in the military. Joint trauma, such as an anterior cruciate ligament (ACL) rupture or meniscal tear, initiates a cascade of events that ultimately leads to inflammation, chondrocyte death, and proteoglycan (PG) loss from the cartilage ECM. Though PG loss alone may be reversible, a majority of patients develop OA 10-20 years later, even if they received surgery to stabilize the joint. Though the mechanisms of PTOA progression are still not entirely known, acute inflammation appears to persist into chronic inflammation, resulting in catabolic breakdown of cartilage, which stimulates inflammation and results in a destructive joint environment. New therapeutic paradigms are needed that address the spectrum of cartilage risk and disease states. This proposal focuses on protecting cartilage after joint injury and preventing chronic inflammation from ensuing by developing drug carriers targeted to cartilage and to the synovial fluid and delivering an anabolic and anti-inflammatory drug, respectively.

The current example provides a foundation for drug delivery systems that takes advantage of specific nanoparticle (NP)-extracellular matrix (ECM) interactions and different modes of access to the joint to effectively localize disease-modifying drugs. In one system, NPs are "painted" onto the cartilage surface during surgical access to the joint, providing sustained release of an anabolic agent after joint injury. This is followed by an injectable system with high joint residence time to minimize macrophage recruitment and activation of the synovium. Preliminary data indicate key NP properties impact binding and retention to extracellular matrix (ECM) molecules in cartilage and synovial fluid, which will be exploited in the design of chondroprotective and anti-inflammatory drug delivery systems, respectively.

Targeted drug delivery can improve drug efficacy and synergy to ultimately slow/stop PTOA disease progression after injury. This is tested by engineering a nanoparticle system for site-specific retention in articular cartilage, engineering a nanoparticle system for prolonged joint residence time in synovial fluid, then combining these methods to evaluate the efficacy of drug-loaded, targeted delivery systems to preserve joint structure and reduce pain in a rodent OA model.

Engineer a Nanoparticle System for Site-Specific Retention within Articular Cartilage.

Joint trauma results in a cascade of mechanical and biochemical events that cause cartilage loss and progresses to PTOA. Drug carriers with high affinity and retention in articular cartilage could provide a means to deliver agents to protect the cartilage after injury. Preliminary data demonstrate significant reduction in NP adhesion to cartilage in the presence of synovial fluid, which will reduce the efficiency of cartilage targeting upon intra-articular injection. Therefore, surgical access to the joint surface during repair of ACL or meniscus damage is used to develop NPs that will rapidly bind and penetrate articular cartilage upon direct application or "painting" to the surface. NP painting can increase site-specific retention within the cartilage compared to intra-articular injection of the same NPs.

NP properties that facilitate rapid binding and long-term retention within cartilage are examined ex vivo, followed by development of an NP painting method and the evaluation of NP biodistribution in vivo.

Determine how NP Size and Surface Functionalization Affect Cartilage Binding and Retention Ex Vivo.

To achieve greater penetration and retention than the 200 nm NPs used in our preliminary studies, NPs with tunable properties based on block copolymers of poly(lactic-co-glycolic acid) and poly(ethylene oxide) (PLGA-b-PEG) are synthesized by nanoprecipitation techniques to form 50-100 nm and 100-200 nm NPs. Three different surface functionalization strategies will also be used to provide different cartilage binding mechanisms, including: 1) PLGA-b-PEG functionalized with cationic dodecyltrimethylammonium bromide (DMAB) to provide electrostatic interactions with GAGs, 2) PLGA-b-PEG functionalized with a collagen type II binding peptide (WYRGRLK (SEQ ID NO:1)) to provide specific biding to the collagen matrix of cartilage, and 3) PLGAb-PEG functionalized with aldehyde groups to provide rapid, covalent (though non-specific) binding to the cartilage tissue on application. The various NP formulations are evaluated for adhesion and long-term retention within cartilage explants, which are cytokine challenged to induce GAG loss and early stage OA. Cytocompatibility of the NP treatment over time is evaluated by Live/Dead imaging.

Establish a "Painting" Method for Delivering NPs to the Cartilage Surface.

NP formulations that demonstrate high retention and cytocompatibility are used to develop a painting method. To determine an acceptable method, the consistency and level of NP retention after application with a surgical sponge and with or without a chondroitin sulfate-based tissue sealant are quantified on explants and cadaveric rat joints.

Evaluate NP Biodistribution In Vivo.

In vivo biodistribution studies compare NP painting with intra-articular injection of cartilage-targeted NPs. Two NP systems are selected as described above from ex vivo studies. A well-established rodent model of OA that surgically simulates a medial meniscus tear (MMT), a common precursor to human OA, is used. Near infrared dye (NIR)-loaded NPs are injected or painted in joints 1 week after MMT, and joint retention monitored by IVIS imaging. Biodistribution of NPs within the joint is assessed after dissection of joint tissues and quantification for labeled NPs. The NP system with the highest in vivo retention in cartage will be used for drug delivery.

Outcomes: Aim 1 will result in an NP platform for cartilage retention on direct application to the cartilage surface. PLGA-PEG systems have ideal properties for these studies because these materials have demonstrated biocompatibility in the joint, can readily encapsulate and release a wide range of therapeutics, and have surface properties that can be specifically engineered independent from the biochemical properties of the encapsulated drug. Therefore, the knowledge gained in the proposed studies can be applied to a wide range of OA therapeutics as well as to other particulate systems used for drug delivery and imaging/diagnostics in the joint.

Engineer a Nanoparticle System for Prolonged Joint Residence Time.

Immune modulation is an important consideration for both disease-modification and symptom management in OA. Particulate systems injected into the joint naturally accumulate in the synovium, which is the site of joint clearance and immune cell recruitment. Prevention of NP uptake in the synovium can increase NP residence time. NPs are designed that can be sequestered in synovial fluid and provide sustained release of anti-inflammatories to the joint space. Preliminary data suggests NP properties can influence binding to synovial fluid constituents and minimize uptake by the synoviocytes, which is exploited for joint space targeting.

NPs are designed for sequestration in synovial fluid by binding to synovial fluid components. Two PLGA-based NP formulations are synthesized to create amine-functionalized PLGA NPs and PLGA NPs with a hyaluronic acid (HA) binding peptide (HAbp; GAHWQFNALTVR (SEQ ID NO:2)). Amine-functionalized NPs consistently formed gels with synovial fluid in preliminary studies, but do not form gels with HA solutions. Therefore, these NP-synovial fluid interactions cannot be attributed to electrostatic interactions with only HA, but have potential for sequestering drug in the joint space.

To explore NP-synovial fluid interactions as a drug delivery target, amine functionalized PLGA NPs are synthesized by conjugating poly(ε-carbobenzoxy-L-lysine) to the PLGA12 followed by double emulsion. To engineer specific interactions with the synovial fluid, HAbp-functionalized PLGA NPs are synthesized using a double emulsion method in poly(vinyl)alcohol (PVA) followed by peptide conjugation via a two-step epoxy method. PLGA NPs conjugated to a scrambled peptide will serve as controls.

Evaluate NP-Synovial Fluid Interactions Ex Vivo.

NP-synovial fluid interactions are evaluated by rheometry to determine the kinetics of gelation. Gel stability and NP release over time are characterized. NP uptake and cytocompatibility with synovial fibroblasts and macrophages are assessed, and compared to "untargeted" control NPs.

Evaluate Joint Retention and Biodistribution of Nanoparticles In Vivo.

Joint retention and biodistribution of NIR dye loaded NPs (amine functionalized, HA-targeted, and non-targeted) are evaluated in the MMT rodent model.

NP targeting to endogenous synovial fluid components can provide prolonged joint retention compared to untargeted NPs. The NP system that provides the longest joint retention is used for delivery of an anti-inflammatory.

Evaluate Efficacy of Drug-Loaded, Targeted Delivery Systems to Preserve Joint Structure and Reduce Pain in Rodent OA Models.

The above steps provide a foundation for localized delivery to cartilage and a foundation for enhanced joint retention. These systems are tested therapeutically. Kartogenin (KGN), a small molecule with demonstrated ability to promote chondrogenesis and protect cytokine-exposed chondrocytes is loaded into NPs for cartilage painting. Preliminary data show KGN-NPs can stimulate MSC chondrogenesis at levels comparable to TGF-β3. Controlling inflammation is also critical to chondroprotection and alleviating symptoms, and though OA is characterized by articular cartilage erosion, pain is often associated with synovial cellularity and thickening, as well as macrophage activation. Moreover, the persistence of macrophage infiltration and activation in the synovium is implicated in the progression from acute to chronic inflammation, pain, and PTOA. Clodronate (CLO), a potent small molecule inhibitor of macrophage activity, is used in NPs designed for joint space targeting. Targeted delivery of KGN to cartilage can promote chondrogenesis and sustained release of CLO in the joint space can reduce synovial inflammation; moreover, the combination of KGN and CLO an synergistically reduce OA pathogenesis beyond that of either drug alone, including reduction of structural damage, synovitis, catabolic activity, inflammation, and pain-related behaviors in a rat OA model.

Evaluate Drug-Loaded NPs Ex Vivo

The NP systems that emerge are loaded with kartogenin (KGN-NP) and clodronate (CLO-NP), respectively, followed by characterization of NP properties and release profiles. KGN-NPs are evaluated for chondroprotection of cartilage explants in the presence of cytokines, and CLO-NPs for macrophage depletion and reduction of cytokine production in synovium explants.

Evaluate Drug-Loaded NPs In Vivo

Dose response and pharmacokinetics of drug loaded-NPs are evaluated individually and compared to free drug in the rat MMT model of knee OA. The long-term efficacy and synergy of combination therapy are evaluated for preservation of joint structure (histology), disease biomarkers in synovial fluid (CTXII and MCP-1), and pain via behavioral metrics. Novel rodent gait analyses developed by the Co-I (Allen) is used to evaluate OA-related symptoms in the rat. Moreover, a novel magnetic capture technology is used to assess intra-articular inflammation (MCP-1) and catabolism (CTX II) by directly isolating molecular targets from the rat knee. These assessments mirror those used in human patients, and thereby close the gap between preclinical and clinical assessments.

NPs can improve localization and retention of the respective drugs, thereby improving efficacy compared to free drug. Though synergy between KGN and CLO has not been previously established, reducing inflammation and preventing cartilage ECM breakdown simultaneously with two different drug mechanisms may result in synergistic effects.

Example 3

Nanoparticles (NPs) have potential to improve drug localization to specific tissues within the joint, including cartilage and synovium. Tissue-specific delivery may permit controlled administration of drugs to target multiple disease mechanisms. There is a poor understanding of how NP properties influence NP interaction with joint tissues and therefore joint retention time post intra-articular injection. The ultimate goal is to determine the ideal properties for a drug delivery platform that will have high joint retention and tissue targeting in order to improve therapeutic efficacy and reduce dosing requirements.

This example examines whether smaller and cationic NPs exhibit greater retention within the cartilage due to electrostatic interactions with the tissue's anionic extracellular matrix components. Synovial fluid may interfere with uptake into cartilage and synoviocytes.

Nanoparticle Formulation

Two nanoparticle formulations were tested. Double emulsion with Poly (lactic co-glycolic acid) (PLGA) demonstrated biocompatibility in joints and has controllable surface charge via surfactants such as polyvinyl alcohol (PVA) and didodecyldimethylammonium bromide (DMAB) (for anionic NPs: 1% PVA; for cationic NPs: 1% PVA+0.2% DMAB).

Commercially available dye-loaded polystyrene NPs of different size and surface charges were also utilized as model NPs to further probe NP-tissue interactions. This included 30 and 200 nm carboxylated (—COOH) NPs (anionic), and 50 and 100 nm aminated (—NH2) NPs (cationic).

Experimental Methods

NP Characterization

Hydrodynamic diameter, polydispersity, and zeta potential were measured via dynamic light scattering. Characteristics were measured in phosphate buffered saline (PBS) and after incubation with synovial fluid (SF).

Ex Vivo NP Interaction Screening Model

A screening method was developed to assess NP interaction with articular cartilage ex vivo. Cartilage was either kept unmodified or enzymatically digested in 0.2% collagenase type II for 30 minutes to mimic structural and biochemical OA conditions. [6] NPs were either constituted in PBS or bovine synovial fluid (SF). Imaging was performed by fluorescence (surface and cross sections) and confocal microscopy.

Results

As shown in Tables 2A and 2B, synovial fluid impacted NP properties, affecting cartilage retention and synoviocyte uptake. The cationic DMAB NPs demonstrated greatest interaction and penetration with cartilage relative to the anionic PVA NPs under all conditions. All NPs experienced a drop in cartilage retention and synoviocyte uptake when incubated with synovial fluid. Synovial fluid adsorbates onto the NP surface may change their interactions with synoviocytes (FIG. 6).

Tables 1A and 1B show mean nanoparticle properties measured by dynamic light scattering for (A) PLGA NPs and (B) polystyrene NPs that were functionalized with carboxylate or amine groups. "Size"=effective hydrodynamic diameter; "Zeta"=zeta potential; "COOH"=carboxylate-functionalized polystyrene; "NH$_2$"=amine-functionalized polystyrene. 1 Could not measure amine-functionalized polystyrene in synovial fluid because of aggregation (see right). *p<0.05 via a student's t-test (n=3).

Synovial fluid (SF) induced aggregation of amine polystyrene NPs into a viscous "gel". At higher NP concentrations, uptake of 0.1 μm COOH polystyrene NPs decreased when in incubated with synovial fluid or NPs pre-coated with synovial fluid components.

Cartilage health and synovial fluid impact NP interactions with cartilage ex vivo.

Healthy cartilage had significantly more NP retention than OA tissue across all polystyrene NPs in saline. NP retention was reduced when particles were incubated in synovial fluid (n=5). Cationic PLGA NPs had significantly more retention than anionic PLGA NPs for both healthy and OA tissue. Similarly to polystyrene NPs, PLGA NPs experienced decreased retention in OA and synovial fluid (SF) conditions (n=5). Control group with no NPs (n=3) had low to no detectable fluorescence. Histological sections stained with red safranin-O and a fast green show that biopsies of fresh cartilage are rich in proteoglycans, and enzymatically digested OA-modeled tissue has proteoglycan depletion on the articular surface of the cartilage. Histology scale bar=100 μm. PBS=phosphate buffered saline. SF=synovial fluid.

Fluorescence microscopy of biopsy cross sections illustrated greater presence and penetration by cationic DMAB NPs relative to anionic PVA NPs. Additionally, healthy tissue retained more DMAB NPs than enzymatically digested OA tissue.

Discussion

Changes to NP properties after incubation with synovial fluid indicate adsorption of charged synovial fluid components onto the NP surfaces. Reduction in cationic PLGA NP interaction with OA tissue is likely related to loss of negatively charged glycosaminoglycans in the cartilage. This loss may weaken any electrostatic attraction with cationic particles and increase tissue porosity, thereby allowing NPs to be flushed out of the tissue during washing. Unlike with PLGA NPs, there was no clear correlation between poly-

TABLE 1A

PLGA NPs with and without synovial fluid coatings

| | Size (nm) | | | Zeta (mV) | | |
|---|---|---|---|---|---|---|
| Formulation | Before synovial fluid | After synovial fluid | % change | Before synovial fluid | After synovial fluid | % change |
| PVA (−) | 297.1 ± 4.1 | 292.1 ± 2.9 | −2% | −17.0 ± 1.8 | −16.5 ± 1.2 | −3% |
| DMAB (+) | 261.5 ± 1.7 | 300.6 ± 1.8 | 15%* | 24.6 ± 0.9 | −10.9 ± 1.9 | −144%* |

TABLE 1B

Polystyrene NPs with and without synovial fluid coatings

| | Size (nm) | | | Zeta (mV) | | |
|---|---|---|---|---|---|---|
| Reported size and functionalization | Before synovial fluid | After synovial fluid | % change | Before synovial fluid | After synovial fluid | % change |
| 30 nm COOH | 58.9 ± 4.7 | 104.7 ± 33.8 | 44% | −45.4 ± 2.3 | −33.6 ± 5.4 | −35%* |
| 100 nm COOH | 203.3 ± 0.3 | 407.8 ± 6.1 | 50%* | −58.0 ± 6.5 | −33.4 ± 0.8 | −74%* |
| 200 nm COOH | 184.2 ± 6.2 | 192.5 ± 1.1 | 4% | −28.1 ± 2.5 | −38.5 ± 1.0 | 27%* |
| 50 nm NH$_2$ | 57.4 ± 2.3 | N/A$^1$ | N/A$^1$ | 25.1 ± 1.5 | N/A$^1$ | N/A$^1$ |
| 100 nm NH$_2$ | 123.6 ± 1.0 | N/A$^1$ | N/A$^1$ | 44.3 ± 2.3 | N/A$^1$ | N/A$^1$ | styrene NP properties and cartilage retention, suggesting that tissue interactions may depend on factors more complex than size and charge.

Example 4

This example includes data from an in vitro study and pilot in vivo study aimed at establishing the methodology for applying the cartilage surface therapy. In vitro results indicate that the nanoparticles and sealant can be directly applied together on the surface of cartilage to improve NP retention into the tissue. Preliminary in vivo results show that the cartilage surface treatment of NPs plus a sealant retains NPs within the tissue for up to 2 weeks at levels comparable to injection in healthy joints. In this study there was no control of injected NPs into OA joints to make a direct comparison with the surface treatment groups, however, the findings do suggest feasibility of the surface therapy technique.

Ex Vivo Evaluation of CSAld on NP Retention in Cartilage

Cartilage was explanted from bovine juvenile stifles, cut into 6 mm diameter×~3 mm height disks, and enzymatically digested to mimic diseased tissue matrix conditions. The articular surface of each explant was incubated for 30 minutes with a nanoparticle (NP) treatment, followed by 3 washes unless otherwise stated. All treatments were taken from the same batch of fluorescently-loaded poly (lactic-co-glycolic acid) (PLGA) nanoparticles with 2% poly vinyl alcohol (PVA), constituted in phosphate buffered saline (PBS), and bath sonicated for 15 minutes prior to use. Lyophilized chondroitin sulfate aldehyde (CSAld) was prepared to 25% w/v in PBS. The treatments, all at a 200 μg NP/explant dose, included:

Control: No CSAld; washed 3× post incubation

Slurry: NPs and CSAld were pre-mixed into a suspension prior to incubation on cartilage; washed 3× post incubation Sequential: NPs were incubated like control treatments, then excess NP suspension was removed and replaced with two 5 minute CSAld incubations; washed 3× post incubation No wash control: same as the control, except excluded the 3 washes post incubation as a comparison to evaluate the "NP trapping" capabilities of other treatments Some explants (n=2) were used for visualization of NP penetration and retention in the cartilage. The cross section of those explants were imaged under a fluorescence microscope with constant exposure time. NP retention within the remaining cartilage explants (n=5) was measured by homogenizing and lyophilizing the tissue, extracting the fluorophore from the lyophilized matrix, and measuring fluorescence by plate reader and comparing to standards prepared under the same processes.

There was no significant difference between "slurry", "sequential", and "no wash control" treatments. Use of CSAld in combination with NPs ("slurry") yielded improved NP retention in cartilage, relative to the control.

In Vivo Pilot Study of CSAld Influence of NP Retention within the Joint

A pilot study was conducted to establish CSAld "painting" technique in vivo and establish parameters for larger-scale studies. On each animal (n=3), the right knee was surgically opened for painting and underwent the Destabilization of Medial Meniscus (DMM) technique, a surgical model to induce osteoarthritis in rats. Surgical sites were flushed with PBS prior to treatment. The left knee received an injection. The treatments, all at 20 μL 10 mg/mL NP and/or 20 μL CSAld, included:

(Animal 1 right) Paint, sequential
(Animal 2 right) Paint, slurry
(Animal 3 right) Paint, control (no CSAld)
(Animal 1 left) Inject, control (no CSAld)
(Animal 2 left) Inject, slurry
(Animal 3 left) Inject, control (no CSAld)

Animals were imaged via In Vivo Imaging System (IVIS) for 7 days and sacrificed after 15 days. Animal #1 was used for histological assessment, Animals #2 and #3 were used for biodstribution imaging.

The surgical window was too small for the insertion applicator tip proposed. Instead of physically "brushing" the treatment onto the cartilage surface, treatments were added dropwise with a syringe over the exposed tissue.

Immediately after surgery, injections, and treatment, fluorescence signals were visible in all knees except #2 right, which was poor because bleeding during surgery flushed away the NPs.

Over time, the signals decayed, showing a majority of signal loss after ~3 days.

After euthanasia on day 15, joint tissues were excised and imaged via IVIS to determine if NPs (1) still resided within the joint despite low signals for whole joint/animal and (2) if the NPs preferentially accumulated in specific joint tissues. Tissues excised included:

EM: extensor mechanism (includes some quadriceps muscle, patellar tendon, patella, patellar ligament, and likely synovium), intra-articular side face up
F: femoral head, chondyle cartilage face up
T: tibial head, plateau cartilage face up
FP: fat pad
M: meniscus Interestingly, when images were taken at day 15, there were still detectable signals in Animal #2, which initially showed almost no fluorescence in the right knee and by day 7 both knees showed no fluorescence from a whole-joint view in IVIS. Quantification of the signal indicated similar levels of fluorescence in extensor mechanism, femur (cartilage), and tibia (cartilage).

While direct comparison of NP dynamics cannot be made between surgeries and injections because of the surgical disruption of the joint space, the two injections (slurry and control) had similar biodistribution. In the painted control (Animal #3 right) the signal was concentrated in the extensor mechanism, which appeared by photograph to be the site of surgical injury. Distribution of NPs in painted joints was similar for all other tissues between paint slurry and pain control.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A drug delivery system, comprising a chondrogenic or chondroprotective agent contained within a nanoparticle and an effective amount of a bioadhesive consisting of a chondroitin sulfate, a hyaluronic acid, or a poly(lactic-co-glycolic acid) and polyethylene glycol block copolymer functionalized with an aldehyde to adhere and seed the delivery vehicle to a cartilage tissue of a subject, wherein the nanoparticle and the bioadhesive are combined into a slurry for co-administration.

2. The drug delivery system of claim 1, wherein the chondrogenic or chondroprotective agent comprises Kartogenin.

3. The drug delivery system of claim 1, wherein the chondrogenic or chondroprotective agent comprises platelet-derived growth factor (PDGF-BB).

4. The drug delivery system of claim 1, wherein the nanoparticle has a mean diameter ranging from 30 nanometers to 300 nanometers.

5. The drug delivery system of claim 1, wherein the nanoparticles are formed from a polymer selected from the group consisting of hyaluronan, chitosan, collagen, gelatin, alginate, polylactic acid (PLLA), polyglycolic acid (PGA), poly(lactic-co-glycolic acid) (PLGA), poly(ethylene glycol), and chondroitin sulfate.

6. The method of claim 1, wherein the bioadhesive consists of chondroitin sulfate aldehyde (CSAld).

7. A method, comprising administering to a joint of the subject the drug delivery system of claim 1.

8. The method of claim 7, wherein the chondrogenic or chondroprotective agent comprises Kartogenin.

9. The method of claim 7, wherein the chondrogenic or chondroprotective agent comprises platelet-derived growth factor (PDGF-BB).

10. The method of claim 7, wherein the bioadhesive comprises consists of chondroitin sulfate aldehyde (CSAld).

11. The method of claim 7, wherein the nanoparticles are formed from a polymer selected from the group consisting of hyaluronan, chitosan, collagen, gelatin, alginate, polylactic acid (PLLA), polyglycolic acid (PGA), poly(lactic-co-glycolic acid) (PLGA), poly(ethylene glycol), and chondroitin sulfate.

* * * * *